United States Patent
Polo

(10) Patent No.: US 10,478,166 B2
(45) Date of Patent: Nov. 19, 2019

(54) LAPAROSCOPIC MORCELLATING RECEPTACLE AND METHODS OF USE

(71) Applicant: Oscar Polo, Portland, OR (US)

(72) Inventor: Oscar Polo, Portland, OR (US)

( * ) Notice: Subject to any disclaimer, the term of this patent is extended or adjusted under 35 U.S.C. 154(b) by 0 days.

(21) Appl. No.: 15/900,758

(22) Filed: Feb. 20, 2018

(65) Prior Publication Data
US 2018/0168676 A1 Jun. 21, 2018

Related U.S. Application Data

(63) Continuation-in-part of application No. 15/382,119, filed on Dec. 16, 2016, now Pat. No. 9,901,329.

(51) Int. Cl.
*A61B 17/00* (2006.01)
*A61B 17/221* (2006.01)
(Continued)

(52) U.S. Cl.
CPC ...... *A61B 17/00234* (2013.01); *A61B 17/221* (2013.01); *A61B 17/32002* (2013.01);
(Continued)

(58) Field of Classification Search
CPC ............ A61B 17/00234; A61B 17/221; A61B 17/3462; A61B 17/32056; A61B 2017/00287; A61B 2017/00292; A61B 2017/2212; A61B 2017/2215; A61B 2017/3466; A61B 2017/3445; A61B 2050/304; A61B 50/31; A61B 50/312; A61B 17/48; A61B 5/150366; B65D 2543/00; B65D 2543/00009; B65D 2543/00324; B65D 2543/00425;
(Continued)

(56) References Cited

U.S. PATENT DOCUMENTS 4,874,258 A * 10/1989 Marino ............ B65D 88/1618
383/111
5,215,521 A 6/1993 Cochran et al.
(Continued)

FOREIGN PATENT DOCUMENTS

WO 2015/084769 A1 6/2015
WO 2016/058086 A1 4/2016

OTHER PUBLICATIONS

Extended European Search Report issued in EP18158667.8 dated Sep. 19, 2018 (9 pages).

*Primary Examiner* — Christopher L Templeton
(74) *Attorney, Agent, or Firm* — Baumgartner Patent Law; Marc Baumgartner

(57) ABSTRACT

A collapsible and expandable receptacle that can be inserted into a patient's cavity through a laparoscopic port (sleeve) is disclosed herein. The receptacle is configured so that when it enters the cavity it can be expanded or opened into the shape of a bowl or cone. A targeted tissue specimen can then be placed inside the expanded receptacle through a central opening which can be closed afterwards. The surgeon has the room and visibility to cut the tissue with a power morcellator and avoid severing the bag or spreading unwanted particulate tissue to other areas inside the patient. Once the specimen has been cut and removed, the empty receptacle can be collapsed and removed out the same tissue removing sleeve.

18 Claims, 24 Drawing Sheets

(51) Int. Cl.
  *A61B 17/32* (2006.01)
  *A61B 17/3209* (2006.01)
(52) U.S. Cl.
  CPC ............... *A61B 17/3209* (2013.01); *A61B 2017/00287* (2013.01); *A61B 2017/320064* (2013.01)
(58) Field of Classification Search
  CPC .......... B65D 2543/00435; B65D 2543/00666; B65D 33/02; B65D 33/04; B65D 85/808; B65D 31/18; B65D 31/005; A61M 1/0209; A61M 1/0213; A61J 1/05
  See application file for complete search history.

(56) References Cited

U.S. PATENT DOCUMENTS

| | | | | |
|---|---|---|---|---|
| 5,279,539 A * | 1/1994 | Bohan | ............... | A61B 17/00234 600/37 |
| 5,352,184 A * | 10/1994 | Goldberg | ............... | A61B 10/04 128/DIG. 24 |
| 5,465,731 A * | 11/1995 | Bell | ............... | A61B 17/00234 600/37 |
| 5,593,413 A * | 1/1997 | Alexander | ............ | A61B 17/442 606/119 |
| 5,735,289 A * | 4/1998 | Pfeffer | ............. | A61B 17/00234 600/562 |
| 5,788,709 A * | 8/1998 | Riek | ............... | A61B 17/00234 606/110 |
| 6,206,568 B1 * | 3/2001 | Wurr | ............... | B65D 88/1612 383/111 |
| 6,228,095 B1 * | 5/2001 | Dennis | ............. | A61B 17/00234 606/114 |
| 6,406,440 B1 * | 6/2002 | Stefanchik | ........ | A61B 17/00234 600/562 |
| RE42,050 E * | 1/2011 | Richard | ............... | A61B 17/221 606/114 |
| 9,550,046 B1 * | 1/2017 | Allen | ................ | A61M 25/1025 |
| 2001/0002437 A1 * | 5/2001 | Pagedas | ........... | A61B 17/00234 606/114 |
| 2006/0200169 A1 * | 9/2006 | Sniffin | ............ | A61B 17/00234 606/113 |
| 2006/0200170 A1 * | 9/2006 | Aranyi | ............ | A61B 17/00234 606/113 |
| 2006/0229639 A1 * | 10/2006 | Whitfield | ......... | A61B 17/00234 606/114 |
| 2007/0135781 A1 * | 6/2007 | Hart | ................ | A61B 17/00234 604/327 |
| 2008/0033451 A1 * | 2/2008 | Rieber | ............. | A61B 17/00234 606/114 |
| 2011/0190781 A1 * | 8/2011 | Collier | ............ | A61B 17/00234 606/114 |
| 2012/0109144 A1 * | 5/2012 | Chin | ...................... | A61B 17/00 606/114 |
| 2012/0158010 A1 * | 6/2012 | Menn | ............... | A61B 17/00234 606/114 |
| 2013/0245636 A1 * | 9/2013 | Jansen | ............ | A61B 17/00234 606/114 |
| 2014/0007885 A1 * | 1/2014 | Gillis | ...................... | A61F 5/566 128/848 |
| 2014/0330285 A1 * | 11/2014 | Rosenblatt | ............. | A61B 17/42 606/114 |
| 2016/0302783 A1 * | 10/2016 | Greenberg | ....... | A61B 17/00234 |
| 2016/0338682 A1 * | 11/2016 | Hoyte | ............. | A61B 17/00234 |
| 2016/0346000 A1 * | 12/2016 | Abreu | ............. | A61B 17/32056 |
| 2017/0144835 A1 * | 5/2017 | Butler | .................... | B65F 1/068 |
| 2017/0215904 A1 * | 8/2017 | Wassef | ................. | A61B 17/32 |
| 2018/0049771 A1 * | 2/2018 | Rhemrev-Pieters | ........................ | A61B 17/00234 |

* cited by examiner

LAPAROSCOPIC MORCELLATING RECEPTACLE AND METHODS OF USE

CROSS-REFERENCE TO RELATED APPLICATIONS

This application is a Continuation-in-Part application which claims the benefit of priority to U.S. patent application Ser. No. 15/382,119, filed Dec. 16, 2016, which is incorporated herein in its entirety.

FIELD OF THE INVENTION

The teachings herein relate to methods and compositions useful in laparoscopic power morcellation. More specifically, the embodiments herein relate to receptacles configured to prevent morcellated particulate tissue, from spreading into nearby areas from the cutting site.

BACKGROUND

Power morcellators are devices, used in laparoscopic surgery that morcellate, or cut tissue, into smaller pieces to allow for removal through small surgical access sites. Currently laparoscopic power morcellation for the removal of the uterus (hysterectomy) or uterine fibroids (myomectomy) in women is discouraged because, based on an analysis of currently available data, it may pose a risk of inadvertently spreading cancerous tissue, notably uterine sarcomas, beyond the uterus. In trying to prevent the potential spread of cancerous tissue, morcellation receptacles have been designed to contain the specimen that is being cut and to remove the severed pieces as they are being cut. Current receptacles for laparoscopic surgery are used for retrieving specimen. They have an expandable and collapsing collar at the opening that is attached to a hanging bag that opens enough to accommodate the targeted tissue. Unfortunately, these current receptacles do not give the surgeon the room or visibility to perform power morcellation within them without the risk of severing the receptacle. Other receptacles are designed for morcellation with a hand-held scalpel as opposed to power morcellation. These receptacles have the opening of the bag external to the cavity so that the tissue inside the receptacle can be visibly severed and removed through the expanded incision on the abdominal wall. An inflatable bag design was recently approved for use with both a handheld scalpel or power morcellator, but this bag's small opening significantly limits the use of a power morcellator and laparoscope because there is not sufficient room for the surgical cutting device to move and cut within the bag. Furthermore, this bag is inflatable and so severing or puncturing this bag would make it ineffective for its intended use. Preferred receptacles herein are not inflatable.

Accordingly, there is a need in the art for receptacles configured to give the medical practitioner (e.g., surgeon) enough room and visibility to perform power morcellation, within them, using the spaced apart laparoscopic ports already in place for the intended surgical procedure and that allows for improved handling and visibility of the specimen and decreases the likelihood of severing the receptacle. The following disclosure describes expanding/collapsing receptacles configured for use with power morcellators that address this need in the art.

SUMMARY

Preferred embodiments are directed to a morcellation receptacle system having: a collapsible receptacle, having a vertical axis with a lower half section with a distal area, and an upper half section with a proximal end, and a horizontal axis, configured such that when the collapsible receptacle is collapsed on its horizontal axis, it is linearly sized to fit within and through an opening between 14-20 mm in width but not when expanded in a natural open position; said receptacle comprising: a distal area; a plurality of at least three support rods positioned in a circumferential and equidistant manner around the vertical axis, or substantially so, and having proximal ends extending proximally and laterally away from the distal area and configured such that the support rods can move towards each other on the horizontal axis when the receptacle is collapsing and move away from each other on the horizontal axis when the receptacle is opening, a flexible liner that is water resistant, low-friction, tear-resistant, and made of material different from the support rods, having a thickness between 0.05-0.15 mm, wrapped along the support rods such as to define a bag with a closed end at the distal area; and a cover that is permanently attached to the perimeter of the proximal end of the receptacle that comprises a substantially central opening wherein said opening is configured to be releasably closable such that at least 75% of the opening's area is occluded, and the cover is expandable and collapsible to fit through the 14 to 20 mm opening.

A method of morcellating a targeted piece of tissue in a subject comprising:
a) providing a collapsible receptacle, having a vertical axis with a lower half section with a distal area, and an upper half section with a proximal end, and a horizontal axis, configured such that when the collapsible receptacle is collapsed on its horizontal axis, it is linearly sized to fit within and through an opening between 14-20 mm in width but not when expanded in a natural open position; said receptacle comprising: a distal area; a plurality of at least three support rods positioned in a circumferential and equidistant manner around the vertical axis, or substantially so, and having proximal ends extending proximally and laterally away from the distal area and configured such that the support rods can move towards each other on the horizontal axis when the receptacle is collapsing and move away from each other on the horizontal axis when the receptacle is opening, a flexible liner that is water resistant, low-friction, tear-resistant, and made of material different from the support rods, having a thickness between 0.05-0.15 mm, wrapped along the support rods such as to define a bag with a closed end at the distal area; and a cover that is permanently attached to the perimeter of the proximal end of the receptacle, is expandable and collapsible to fit through the 14 to 20 mm opening, and comprises a substantially central opening;
b) creating one or more incisions in the subject near the targeted piece of tissue, wherein the incision has a width of between 14-20 mm and inserting a first trocar sleeve into a first incision;
c) collapsing the receptacle;
d) inserting the collapsed receptacle inside of the subject through the first trocar sleeve;
e) positioning the targeted tissue into the receptacle through the central opening in the cover;
f) closing the central opening such that at least 75% of the opening's area is occluded;
g) positioning a morcellator into the receptacle and cutting the target tissue;
h) removing the cut targeted tissue from the receptacle through a trocar sleeve; and i) collapsing the receptacle and withdrawing it from inside the subject through a trocar sleeve.

BRIEF DESCRIPTION OF THE DRAWINGS

It will be appreciated that the drawings are not necessarily to scale, with emphasis instead being placed on illustrating the various aspects and features embodiments of the invention, in which.

DETAILED DESCRIPTION OF THE ILLUSTRATED EMBODIMENTS

Embodiments of the present invention are described below. It is, however, expressly noted that the present invention is not limited to these embodiments, but rather the intention is that modifications that are apparent to the person skilled in the art and equivalents thereof are also included.

Figure 1:
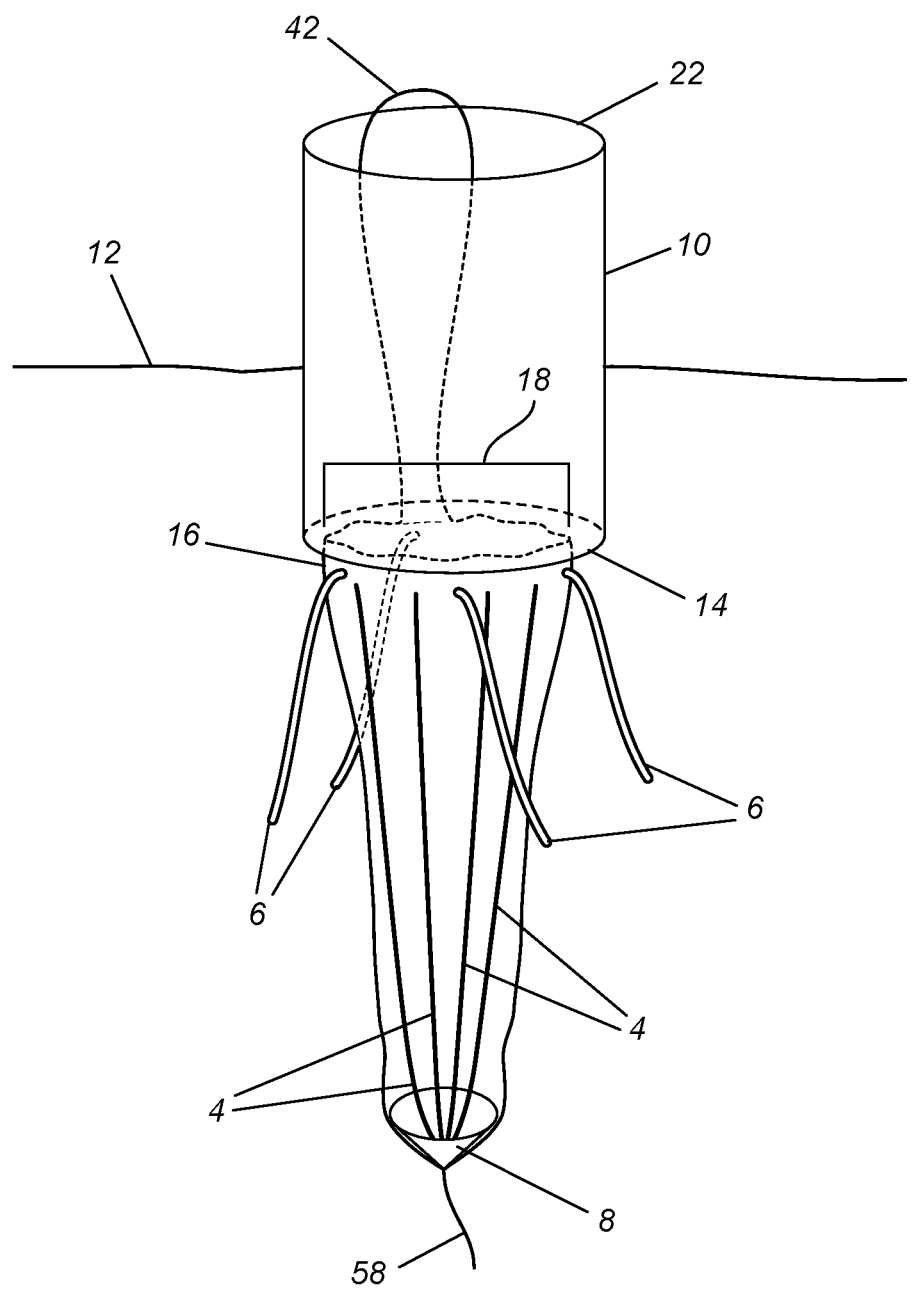
FIG. 1 is a perspective view of a collapsed receptacle passing through a trocar sleeve penetrating a patient's abdominal wall.
Figure 2:
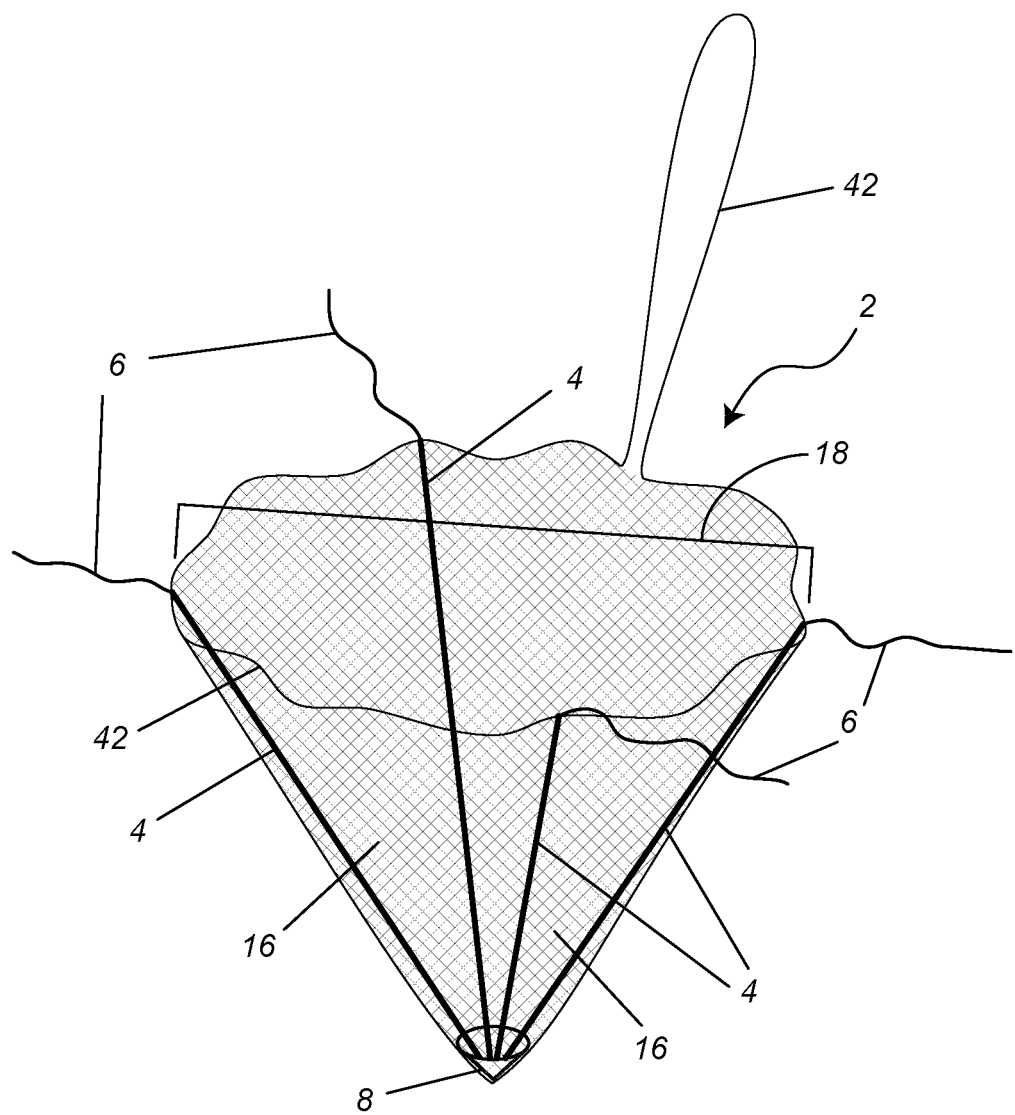
FIG. 2 is a perspective view of an opened receptacle having straight support rods coupled to filaments.

FIGS. 1 and 2 show the receptacle 2 in a collapsed/closed position and an open position respectively. The collapsed configuration shown in FIG. 1 and the open configuration of FIG. 2 both depict the receptacle 2, having a plurality of support rods 4 coupled to a distal base 8. The receptacle 2 has a vertical axis with a lower half section and a distal end, and an upper half section with a proximal opening 18.

Figure 3:
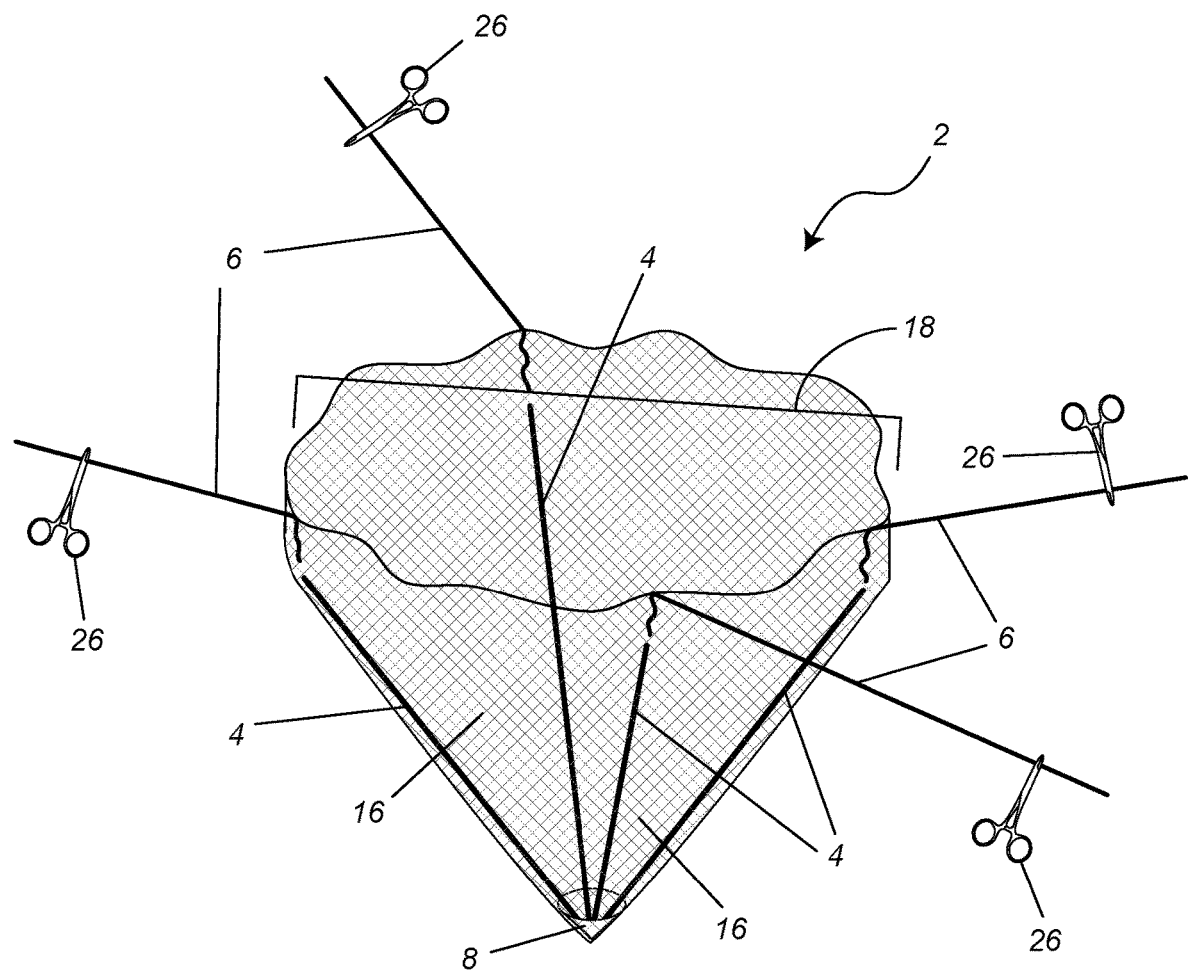
FIG. 3 is a perspective view of an opened receptacle having straight support rods not coupled to filaments.

In FIG. 1, the closed receptacle 2 is shown passing through the inside of a trocar sleeve 10, which can non-exclusively include any suitable laparoscopic port or sleeve used in surgery. The receptacle has a liner 16, made of a thin, flexible material that is fluid impermeable, and preferably is hypoallergenic, has a low coefficient friction, and is made of a tear-resistant material such as ripstop nylon, polyurethane, or polyisoprene. Latex could be a suitable material as well, such as for situations where neither the patient nor medical practitioner is allergic. The flexible liner 16 is wrapped along the support rods 4 (it can be on the outside and/or inside of the rods 4) such as to define an enclosed space, or bag, with a proximal opening 18 defined by proximal/upper portion of the flexible liner 16. According to preferred embodiments, such as when the rods 4 are flexible, they can maintain the shape of the open receptacle 2, such as a bowl shaped, for example. According to further embodiments, the rods are coupled to the bag in a direction which keeps the rods from sliding right or left. In FIG. 1, the proximal ends of the support rods 4 traverse up from the distal base 8 to the proximal opening 18. This is merely optional, however. As an alternative, the support rods 4 only traverse up to the upper proximal section of the flexible liner 16, such as shown in FIG. 3. Advantageously the flexible liner 16 creates a waterproof seal, water resistant, or impermeable barrier to blood or particular tissue around the working space, with the exception of the proximal opening 18. Thus, according to certain embodiments, the proximal opening 18 is the only opening, or access point, of the receptacle 2. According to further embodiments, such as shown in FIGS. 16-21, a covering (e.g., lid 46') can be placed over the proximal opening 18 wherein the covering has a central opening 68 configured to allow a specimen to pass through, and that can be covered, or substantially so.

The trocar sleeve 10 is positioned through a patient's outer body, or more specifically their abdominal wall 12 such that its proximal opening 22 is located outside of the patient which leads through the hollow trocar sleeve 10 to a distal opening 14 within the patient's body, or more specifically their abdominal cavity. According to preferred embodiments, in the collapsed configuration, the receptacle 2 has a small enough width or diameter to fit within the trocar sleeve 10 and pass through the proximal and distal openings 22 and 14. Preferred embodiments of receptacles 2 can fit through a trocar sleeve 10 having a hollow internal channel with a diameter or width of about 15 mm, such as 10-20 mm. These dimensions are also applicable for the proximal and distal openings 22 and 14 of the trocar sleeve 10. This configuration can be accomplished using any suitable dimensions, for example, by measuring or approximating the width of the collapsed rods 4, so that at maximal measurement or approximation of the diameter of collapsed rods 4 is less than the diameter/width of the hollow channel within the trocar sleeve 10. Suitable diameters/widths of the collapsed rod can thus be about 14 or 14.5 mm including between 9-19 mm. Similarly, the distal base 8 should be sized to likewise fit though the hollow channel within the trocar 10 and its proximal and distal openings 22 and 14. Thus, in general, the distal base's width/diameter should be less than the diameter/width of the hollow channel within the trocar sleeve 10, including the proximal and distal openings 22 and 14. These widths/diameters can be about 14 or 14.5 mm including between 9-19 mm. Embodiments herein further contemplate instances where the rods 4 and/or distal base 8 are made of flexible or elastic material, and their widths/diameters in a closed configuration could be the same or larger than the width/diameter of the hollow channel within the trocar sleeve 10, including the proximal and distal openings 22 and 14, so long as the rods 4 and distal base 8 can further compress/collapse to pass through the trocar sleeve. As a non-exclusive example, the support rods 4 and/or the distal base 8 can be made of an elastic material such as nitinol, also known as nickel titanium.

Figure 4A:
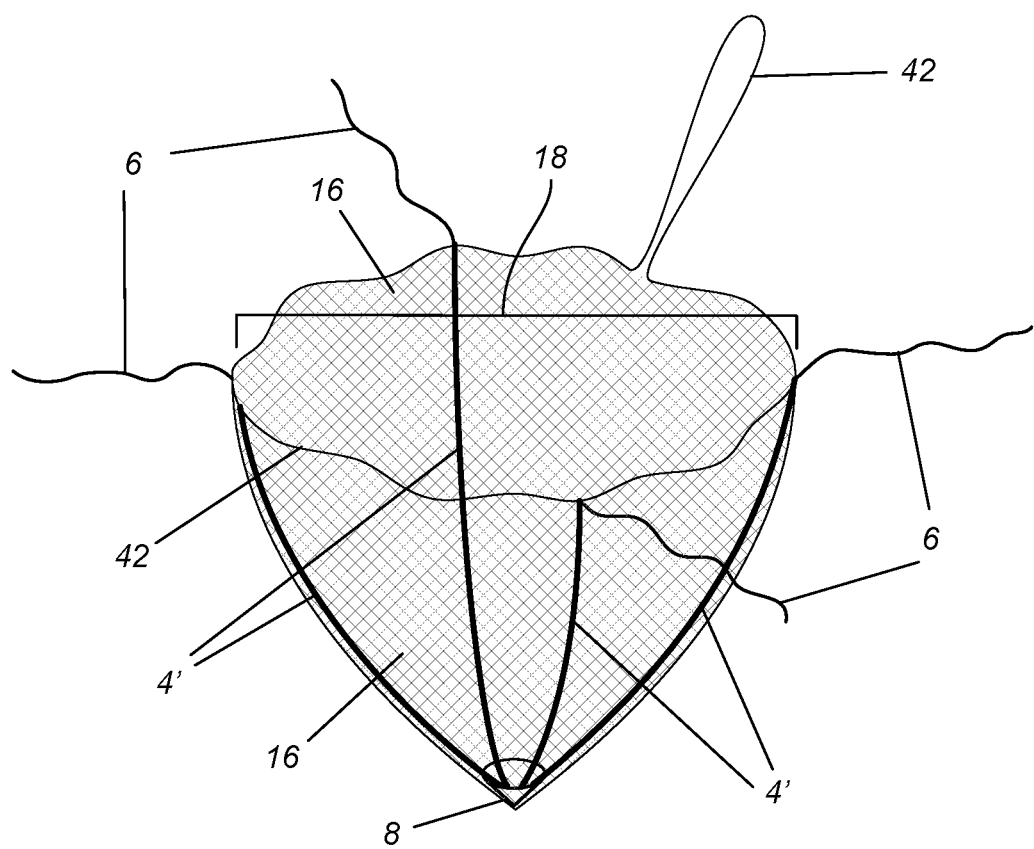
FIG. 4A is a perspective view of an opened receptacle having a drawstring and concave support rods coupled to filaments.
Figure 4B:
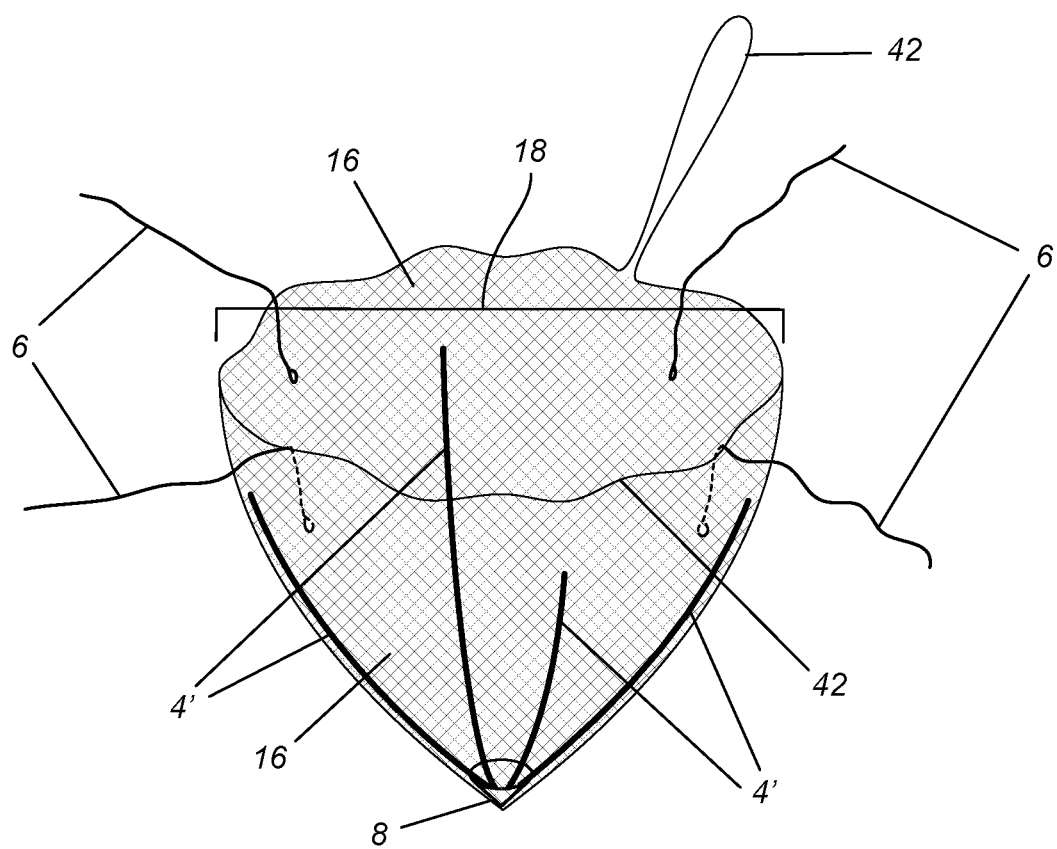
FIG. 4B is a perspective view of an opened receptacle having a drawstring and concave support rods not coupled to filaments.
Figure 10:
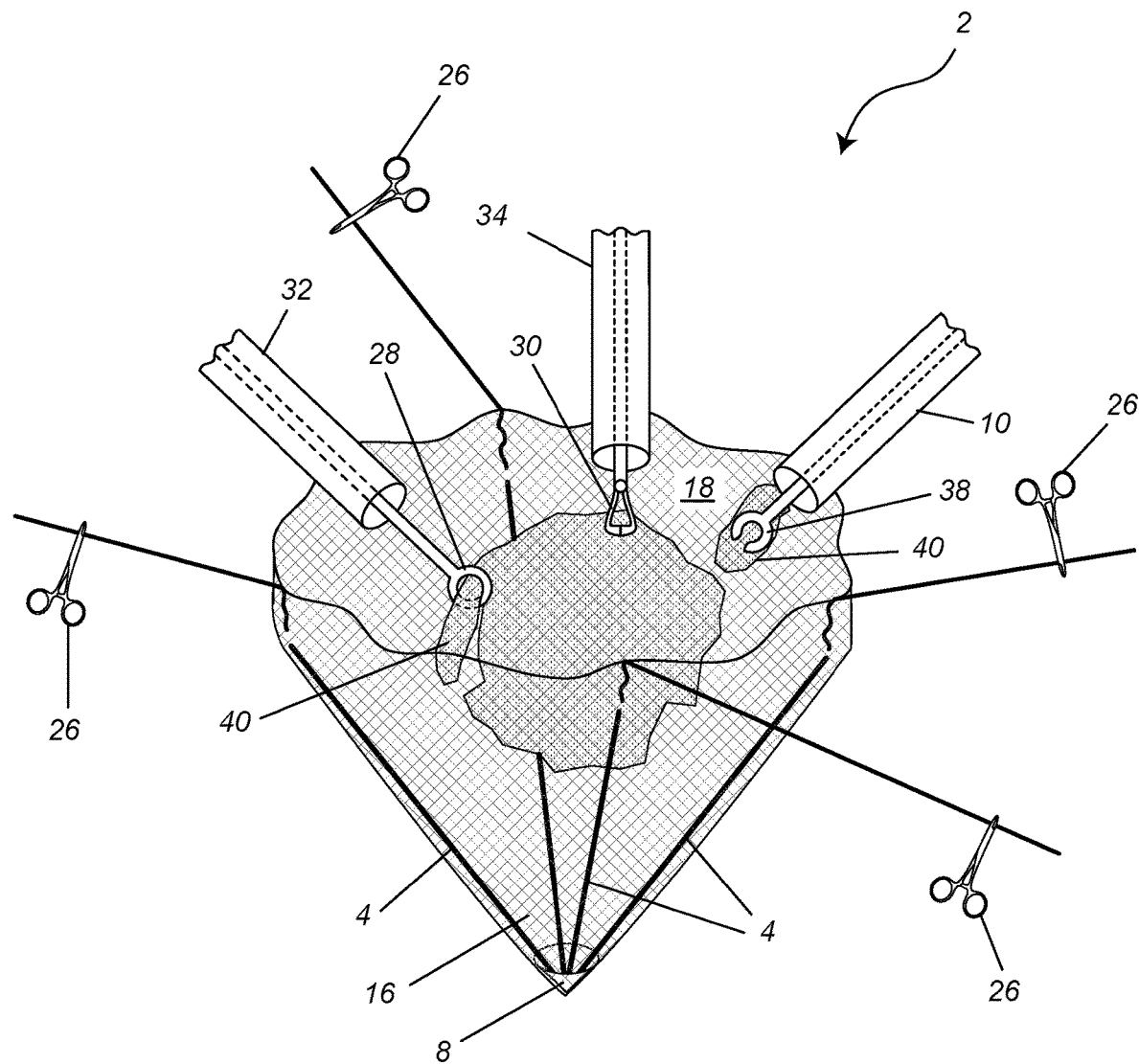
FIG. 10 is a perspective view of a tissue sample being morcellated and removed within an opened receptacle.
Figure 11:
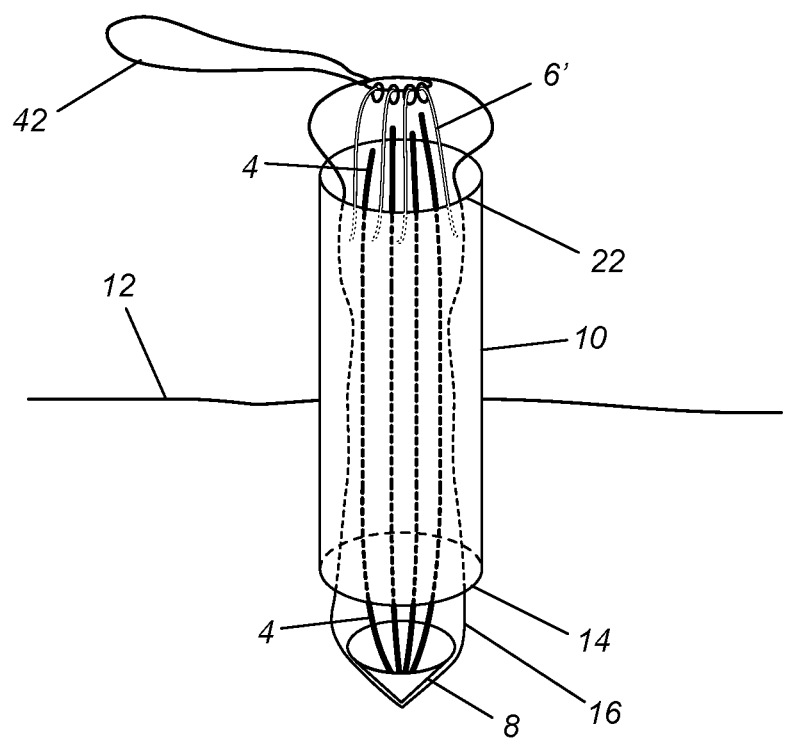
FIG. 11 is a perspective view of a collapsed receptacle having a draw string and positioned within a laparoscopic sleeve penetrating a patient's abdominal wall.

As shown in FIG. 2, the receptacle 2, in its open position, is shaped as a cone or bowl, for containment of the specimen, trocar sleeves, and surgical instruments, such as graspers, laparoscopes, and the morcellator. While non-limiting, it is preferred that the receptacle 2 is in a bowl shape rather than a funnel shape to accommodate the specimen 40 better. The receptacle 2 can also be cone shaped or concave as well. A main objective of the present embodiments is to provide a receptacle 2 that is small enough to travel through a trocar sleeve 10 (whether through insertion or extraction), yet also expand large enough to surround a working space which can include a target specimen 40 and multiple trocar sleeves and instruments for cutting, grasping, viewing, and extracting the specimen from the patient. FIG. 10 is an exemplary figure showing various instruments 28, 30, 38 grasping and cutting a specimen 40 that the receptacles 2 herein are configured to surround when positioned inside a patient. Accordingly, preferred proximal opening 18 diameters are between 14-30 cm, when the receptacle 2 is in an open position, such as shown in FIGS. 2 and 10. The proximal opening 18 can be of any suitable shape to accommodate the specimen 40 and desired instruments, such as circular or oval, for example. The proximal half of the cone shaped bag can include a collar of 2-5 cm in length that is made of the same fabric that is continuous with the vertical axis of the bag and maintains the shape throughout its length. In FIG. 4B, the area of liner 16 between the proximal ends of the rods 4 and the proximal opening 16 can be considered the collar.

In FIG. 2, the receptacle 2 has a distal base 8 that is operably coupled to a plurality of support rods 4 which extend to proximal ends that define a proximal opening 18 of the receptacle 2. In other embodiments, the support rods 4 and 4' do not extend to the proximal opening 18, such as shown in FIGS. 3 and 4B. In FIGS. 3 and 4B, the support rods 4 and 4' extend proximally to the upper half of the receptacle 2, but not to the perimeter of the proximal opening 18. While discussion herein is primarily directed to support rods 4, those with skill in the art will appreciate that disclosure herein pertaining to these features are readily interchangeable to other shapes of support rods, such as support rods 4', where suitable. The distal base is also couple to the distal end of the liner.

The proximal ends of the support rods 4 and are configured to move towards each other when the receptacle 2 is collapsing and move away from each other when the receptacle 2 is opening. According to preferred embodiments, the receptacle 2 has a frame of (3-8) of axial support rods 4 that are circumferentially, attached to the distal base 8, preferably at equidistant lengths from each other. These numbers are non-limiting, but preferably four rods 4 are used. The support rods 4 can be shaped in any suitable manner, non-exclusively including straight rods, or curvilinear, such as concave and convex rods, and other suitable shapes, when in the expanded position. FIG. 2 shows an open receptacle 2 having straight support rods 4 that distally converge from their proximal ends to the distal base 8. FIGS. 4A and 4B show an open receptacle 2 having concave support rods 4' that distally converge from their proximal ends to the distal base 8. Additionally, the support rods 4 can non-exclusively be: rigid, adjustable, hinged, jointed, telescoping, flexible, or elastic. Preferably the rods 4 have a natural spring tension that allows them to expand outward when not confined within the trocar sleeve 10 and to collapse inward when traveling through the hollow channel of the trocar sleeve 10.

Figure 4C:
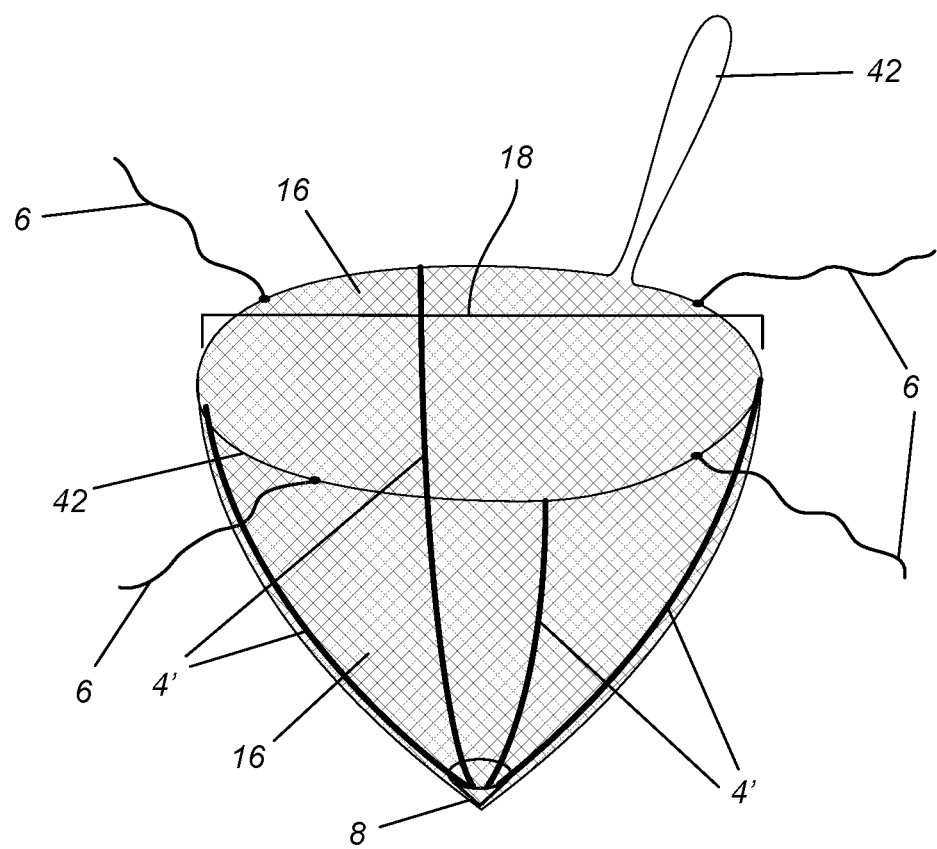
FIG. 4C shows a perspective view of an opened receptacle having drawstring, preferably made of nitinol wire.

FIGS. 1 and 2 also show a drawstring 42 that circumnavigates around the vertical axis of the proximal opening 18 of the receptacle and configured such that when the drawstring 42 is tightened, the opening of the receptacle narrows; the proximal ends of the support rods move toward each other, thereby collapsing the receptacle on its horizontal axis. The drawstring 42 can be coupled to the flexible liner 16 using any suitable way, such as threading the drawstring 42 through loops or a channel within the liner 16 or weaved/threaded through the liner 16 itself. The drawstring 42 can be tightened using any suitable method, such as pulling it in a proximal direction whether manually or with an instrument. Conversely, when the drawstring 42 is loosened, the proximal ends of the support rods move away from each other, thereby expanding the bag to its open position, such as shown in FIG. 2. The drawstring 42 can be made of any suitable material that either has elasticity or does not and will aid in expansion of the proximal end and help maintain the liner 16 on the proximal end from folding on itself when in the open position such as nylon, or thin nitinol, such as 0.25 mm caliber nitinol. FIG. 4C shows a drawstring 42 that is made of nitinol and wherein the filaments 6 are not attached to the rods 4' but the perimeter of the proximal opening 18. According to further embodiments, the drawstring 42 is not elastic, and the rods and filaments are configured to keep the proximal end expanded.

The receptacles herein have a plurality of at least three, or four, support filaments 6 having distal ends coupled to the upper half section of the receptacle in a circumferential manner and configured such that when proximal ends of the support filaments are pulled away from each other, the receptacle 2 is moved in a proximal direction and is maintained in an open position. According to preferred embodiments, the proximal ends/sections of the filaments 6 are brought out of the anterior abdominal wall and can be anchored using any suitable device such as pins or clamps 26 to stabilize the receptacle 2 and maintain it in its open position, such as shown in FIG. 10. The filaments 6 can be spaced apart equidistant around the receptacle 2, (e.g., 90 degrees apart from each other) see FIG. 14 square configuration, or otherwise sufficiently apart from each other, such as at least 45 degrees from each other around the circumference of the receptacle 2. The filaments 6 can be a string or made of any suitable material with elasticity that are configured to stand erect in their natural position for easier grasping by the surgeon. Preferred filaments 6 are connected to the proximal end 18 of the receptacle 2 and not weaved through the collar, to prevent the receptacle 2 from folding in on itself. Preferred filaments 6 are made of thin nitinol, including 0.25 mm caliber nitinol.

According to certain embodiments, the proximal sections of the rods 4 can be coupled to filaments 6 (see FIGS. 2 and 4A) such that when pulled close inwardly, the rods 4 collapse so that the receptacle 2 can pass through the trocar 10 whether being inserted or extracted. Likewise, by pulling the proximal end of the rods 4, such as through pulling the filaments 6 outwardly, the proximal sections of the rods 4 diverge during opening. The filaments 6 can be coupled to any part of the upper half section of the receptacle 2, including the proximal sections of the rods 4, the flexible liner 16, or the rim around the proximal opening 18 of the receptacle, using any suitable way, including adhesives, tying, heat, etc.

Figure 14:
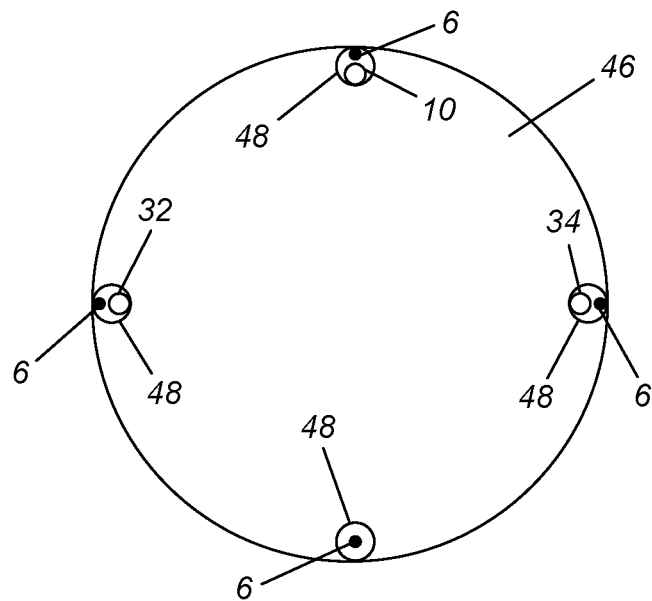
FIG. 14 shows a top view of a lid with four holes spaced equidistantly along the perimeter of the lid (e.g., 90 degrees apart), in a square or diamond configuration.
Figure 15:
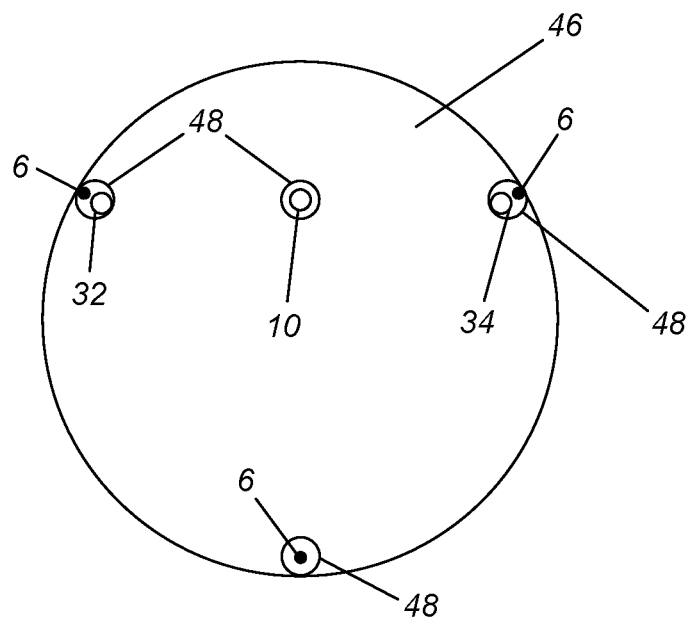
FIG. 15 shows a top view of a lid with four holes spaced apart. The three filaments and their respective holes form a triangle, that is preferably equilateral such that the filaments are equidistant apart from each other with respect to the triangular formation as opposed to their position on the perimeter of the lid.

For purposes of this description there are preferably two to four filaments 6, but more support filaments can be attached and anchored anteriorly, to stabilize the receptacle 2 during morcellation. Even more preferably, the embodiments herein use 3 or 4 filaments 6 spaced apart from each other equidistantly. Additionally, FIG. 14 shows four filaments 6 spaced every 90 degrees around a circular lid 46. FIG. 15 shows three filaments that aren't arranged equidistantly apart from each other around the perimeter of the lid 46, but form a triangle, which could be an equilateral triangle. For both FIGS. 14 and 15 the trocar 10 is preferably inserted through the navel of the patient.

Figure 5:
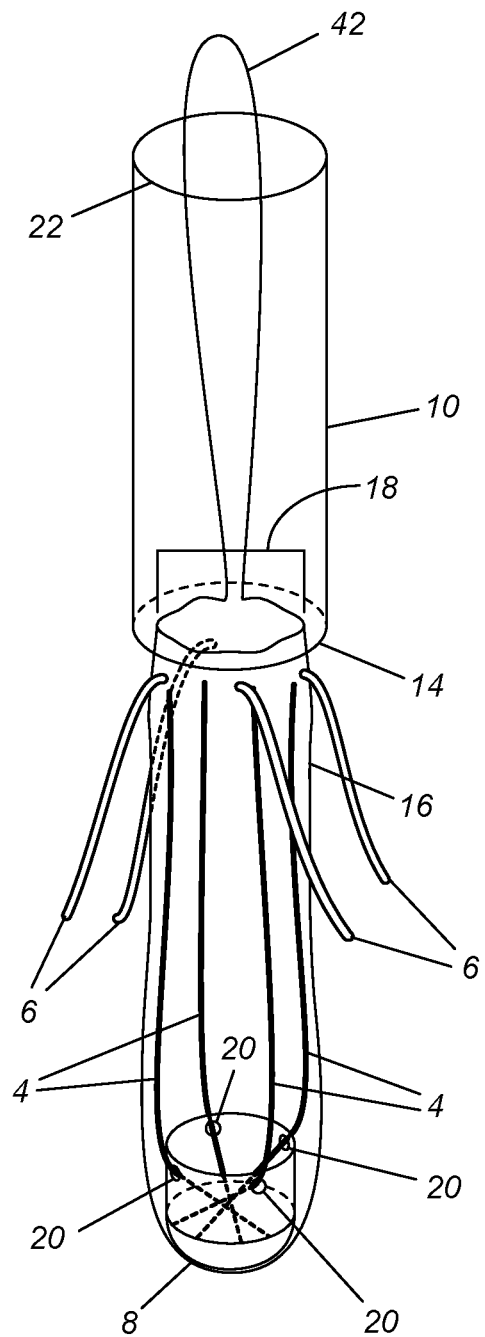
FIG. 5 is a perspective view of an alternative collapsed receptacle passing through a trocar sleeve and having rods that couple to the distal base.
Figure 6:
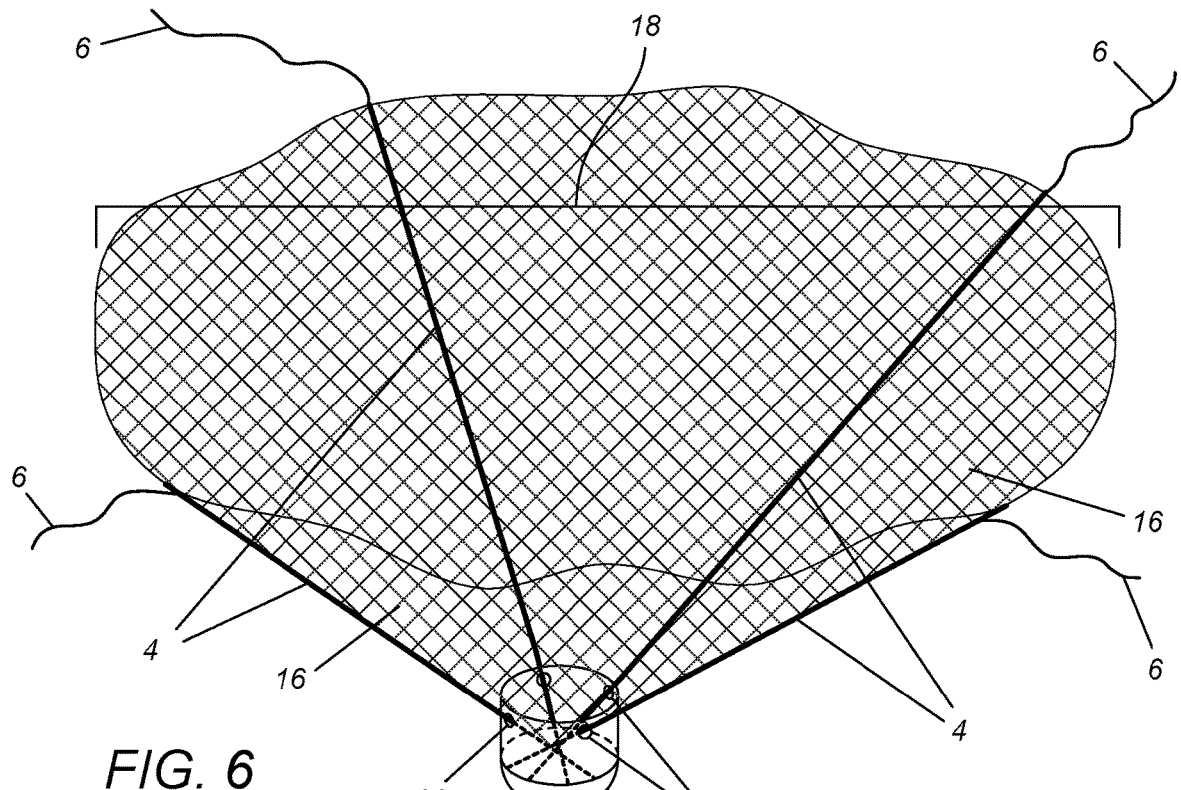
FIG. 6 is a perspective view of an opened receptacle of FIG. 5.
Figure 7:
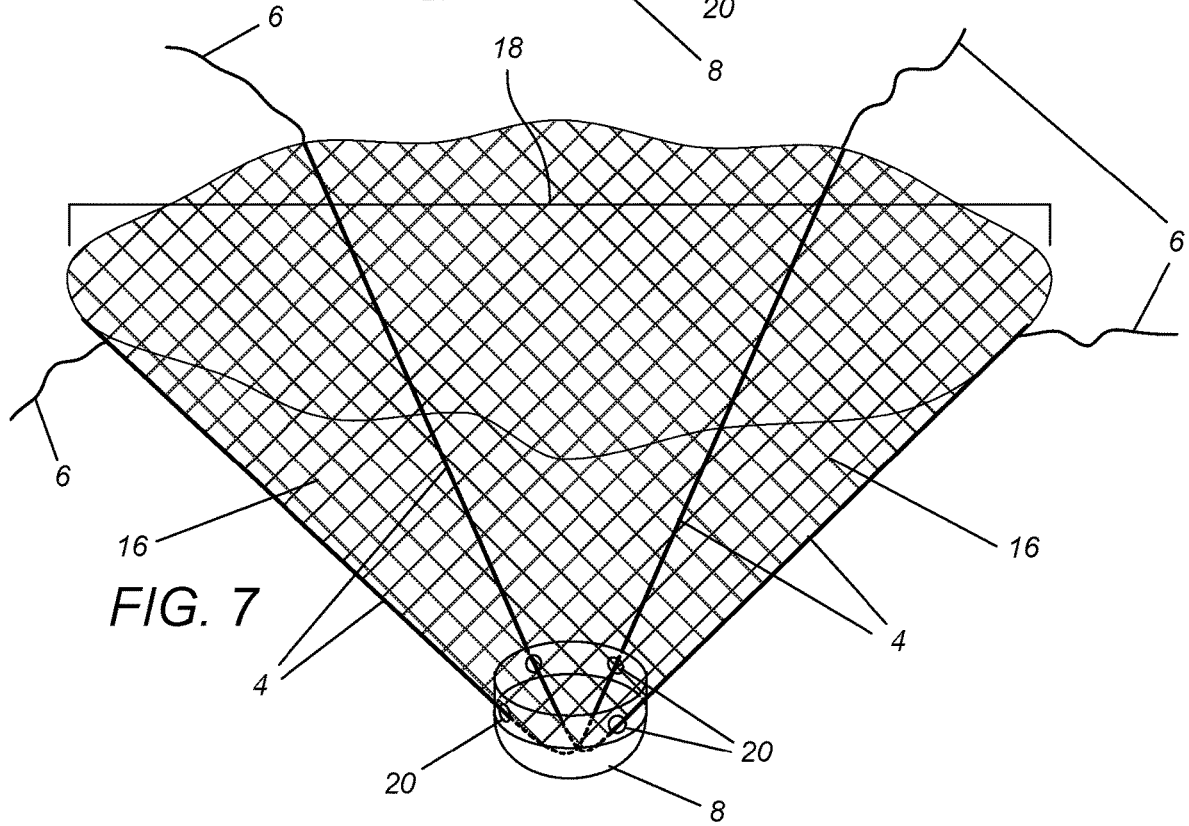
FIG. 7 is a perspective view of an opened receptacle having 2 rods that bend through the distal base.
Figure 8:
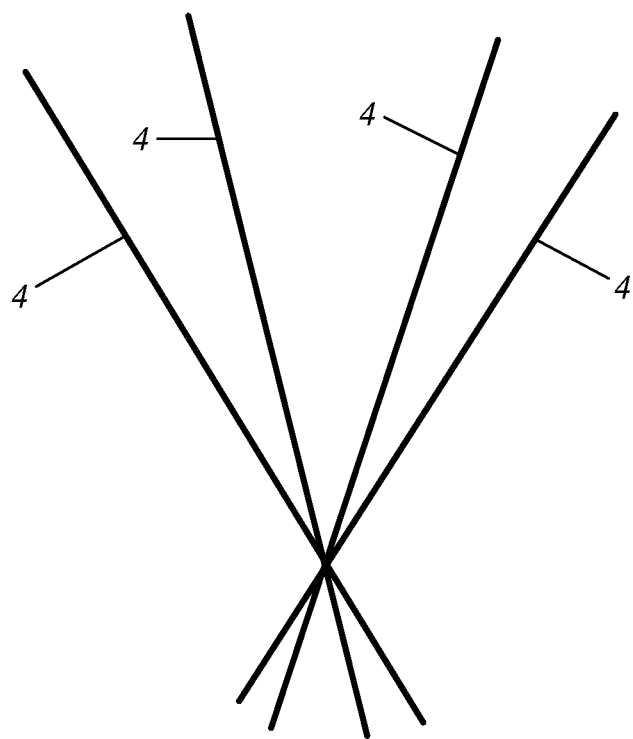
FIG. 8 is a perspective view of the rods in the receptacle shown in FIGS. 5 and 6.
Figure 9:
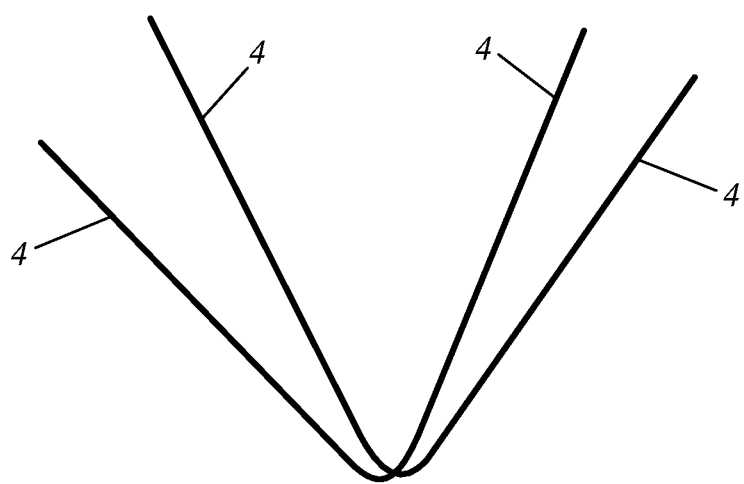
FIG. 9 is a perspective view of elastic rods that bend through the distal base of the receptacle shown in FIG. 7.
Figure 12:
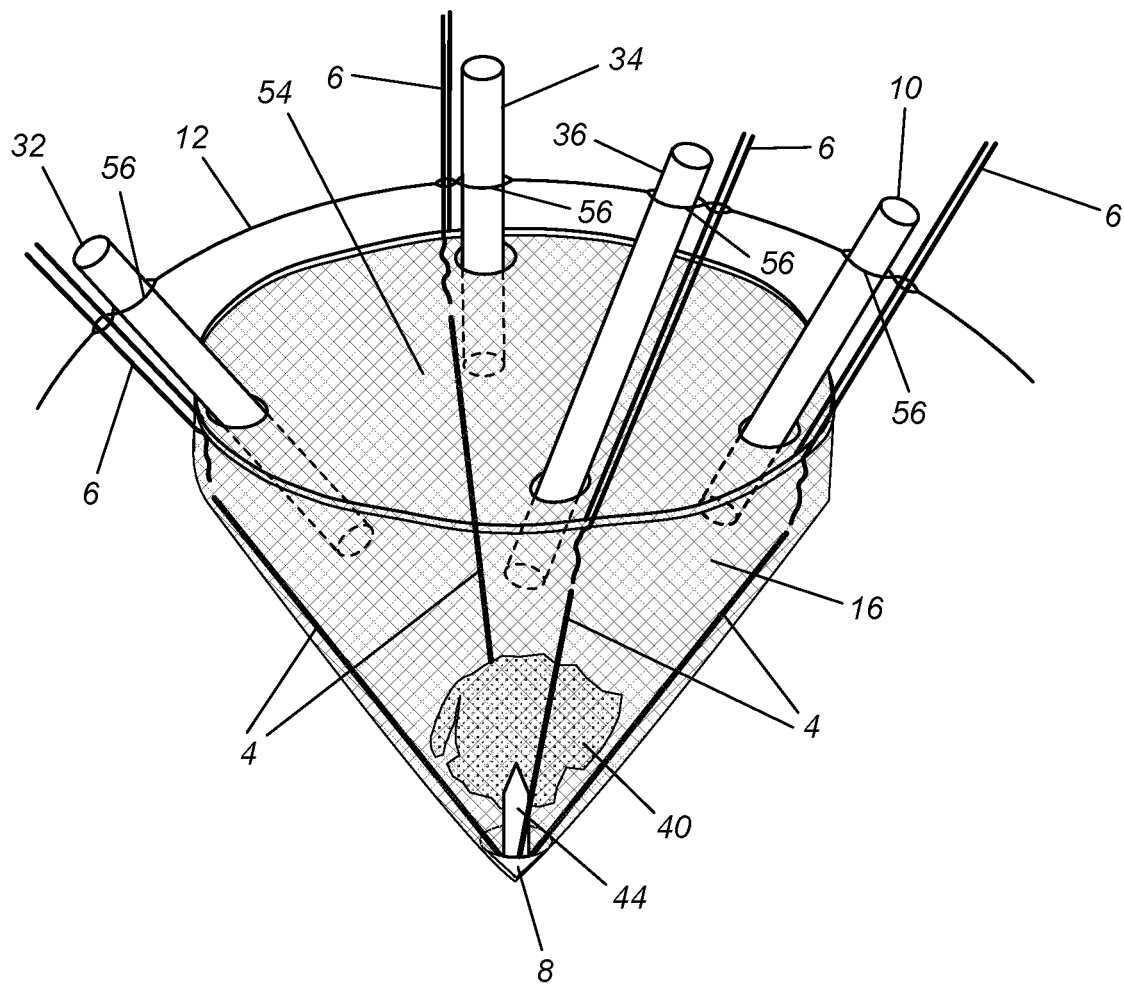
FIG. 12 is a perspective view of an open receptacle having a membrane cover penetrated by four laparoscopic sleeves.

The distal sections of the rods 4 can be coupled to the distal base 8. While the rods 4 described herein can couple to the distal base 8 in any suitable way, FIGS. 5 and 6 depicts a half-capsule shape (half of a spherocylinder) distal base 8 having apertures 20 configured for receiving the distal sections of the rods 4. FIG. 8 is a close-up view of the distal sections of the four rods 4 that couple to the distal base 8 shown in FIGS. 5 and 6. In contrast, FIG. 7 also depicts a half-capsule shape (half of a spherocylinder) distal base 8 having apertures 20 configured for receiving the distal sections of the rods 4. According to this embodiment, the rods 4 curve through the distal base 8, thereby providing natural spring tension when the rods 4 are compressed within the trocar 10 so they can spring open upon passing through the trocar's distal opening 14. FIG. 9 is a close-up view of the distal sections of elastic rods 4 that do not connect to the distal base 8, but rather form a U or V-shape. FIG. 10 shows a targeted tissue specimen 40 and multiple instruments grasping and cutting it within an open receptacle 2. The tissue grasper 38 can serve two purposes: one to help stabilize the tissue 40 as it is being cut and the other is to pull the cut pieces out of the patient, such as through the main trocar sleeve 10, which can be any suitable size, but is preferably 15 mm, or 10-20 mm. The power morcellator 28 is shown cutting the tissue specimen 40 and is positioned through a trocar sleeve 32 that is preferably about 8 mm (e.g., 5-8 mm) in diameter, but can be any suitable size. A second tissue grasper 30 traversing through its trocar sleeve 34 is shown that can optionally help stabilize the tissue specimen 40 during morcellation. This trocar sleeve 34 is preferably about 8 mm in diameter but can be any suitable size. Additional instruments can likewise be utilized within the open receptacle 2, such as a laparoscope. FIG. 12 shows a fourth trocar sleeve 36 that a laparoscope or other instrument can be traversed though. The fourth trocar sleeve 36 can be any suitable diameter such as 5 mm, for example.

In FIG. 12, the proximal opening 18 of the receptacle 2 is covered by a membrane lid 54, that is collapsible when the receptacle 2 is in a closed position, and can expand, or flatten out, when the receptacle 2 opens. The membrane 54 is thin enough that trocar sleeves 10, 32, 34, and 36 can be pressed down manually and puncture the membrane at holes 56, such that the instruments 28, 30, and 38 can be positioned into the open receptacle 2. Any suitable number of trocar sleeves can puncture the membrane 54 depending on the circumstances. For example, 2-6 trocar sleeves could be used to puncture the membrane 54. FIG. 12 also shows a spike 44 that extends proximally from and is operably coupled to the distal base 8. According to these embodiments, the user can pierce the tissue specimen 40 onto the spike 44 thereby helping to stabilize the tissue 40 during cutting.

Figure 13:
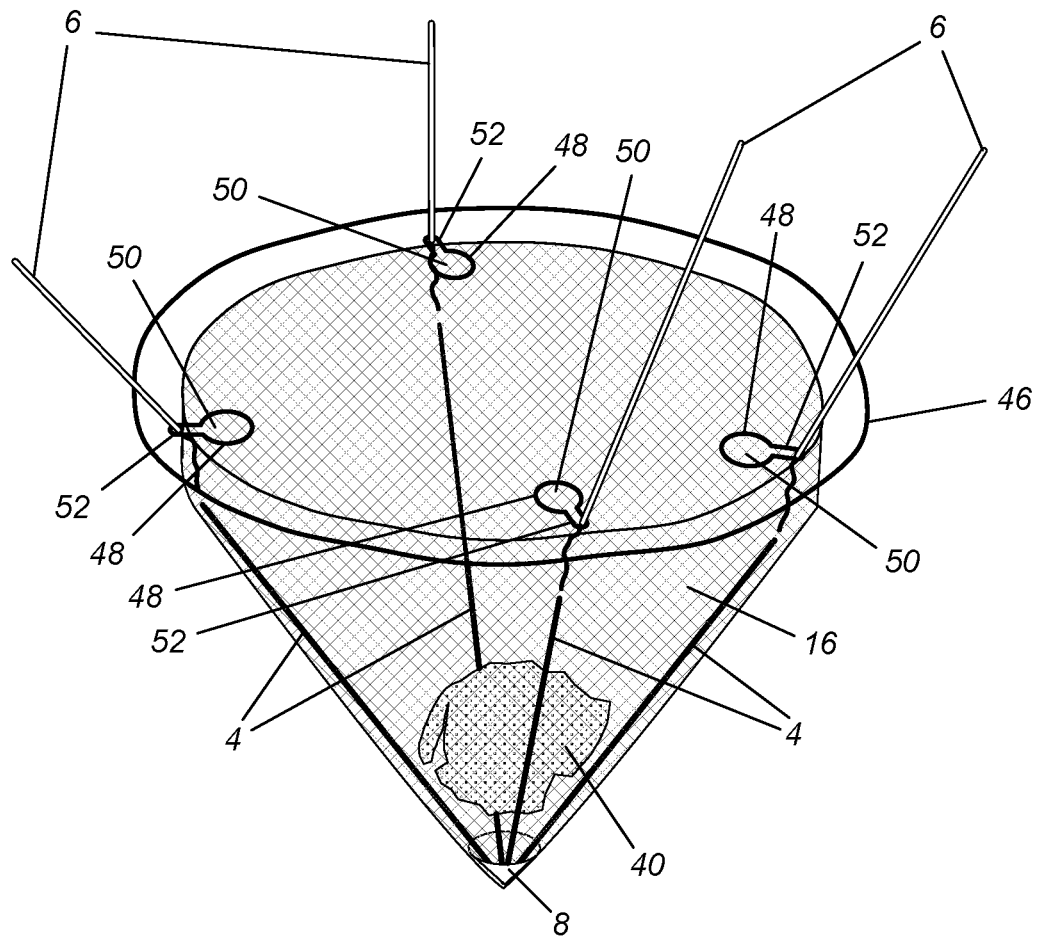
FIG. 13 is a perspective view of an open receptacle having a lid with premade holes configured to receive laparoscopic sleeves and the filaments.

FIG. 13 shows a lid 46 that covers the proximal opening 18 of the receptacle 2 and is collapsible and can expand (flattens out) when the receptacle 2 opens. The lid 46 can be identical to the membrane lid 54 with the exception that it has premade holes 48, and is interchangeable with the embodiments herein, where suitable. The lid 46 is thin and can either be separate/removable from the receptacle 2 or permanently attached to the receptacle 2. Preferably, the lid is sized to fit through an opening of between 14 to 20 mm when collapsed, but not when expanded in its natural open position. The lid 2 can comprise an elastic ring made of 0.6 mm nitinol and is covered by a thin elastic material such as 1 to 3 mil gauge polyurethane film. The lid 46 includes premade holes 48, in contrast to the penetrable membrane 54. The openings 48 in FIG. 13 can be cut in any suitable shape but are preferably configured to receive at least the trocar sleeves 10, 32, 34, and 36 and preferably also the filaments 6. The number and size of the openings 48 can readily be modified depending on the number of trocar sleeves or instruments desired in the working space within the receptacle 2. This number can be 2-6, for example. Preferred openings 48 in the lid 46 are configured to receive both trocar sleeves and the filaments 6. As shown in FIG. 13 the openings 48 are shaped made in a keyhole shape, having both large 50 and smaller 52 sections. The trocar sleeves, e.g., 10, 32, 34, and 36 can pass through the larger holes 50 while the filaments 6 can pass through the smaller sections 52. The openings 48 can be keyhole shape or other shapes such as slits. Additionally, any suitable number of openings 48 can be used to match and accommodate the number of trocar sleeves and/or filaments. According to preferred embodiments, the size of the openings 48 are sized to receive their designated trocar sleeve. According to preferred embodiments the filaments 6 can be configured to align the trocar sleeves with their designated openings 48.

Figure 16:
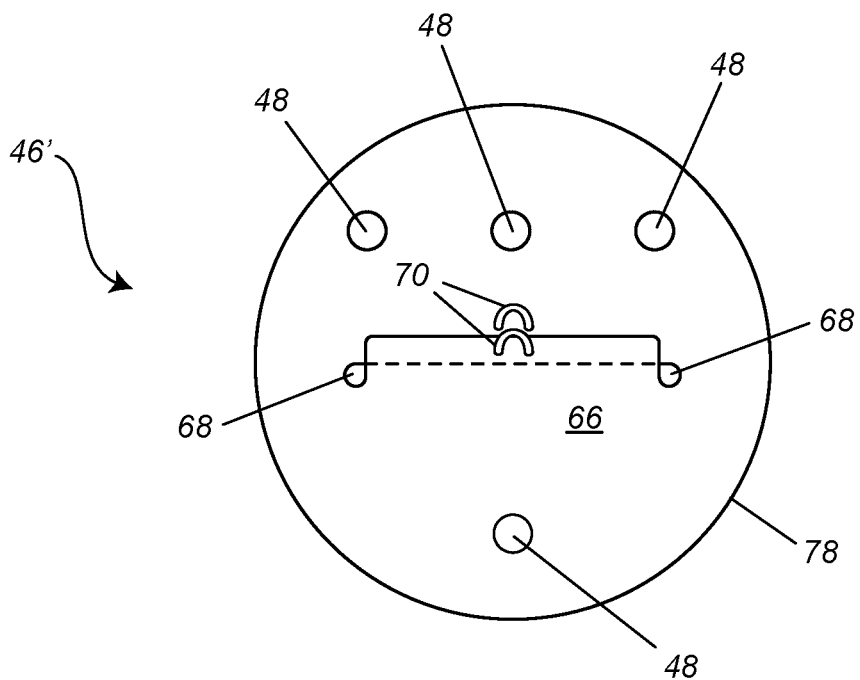
FIG. 16 shows a top view of an alternative lid.

FIG. 16 shows a non-removable, non-hinged, or permanent lid 46' covering the receptacle with premade holes 48 and an outer ring which can be a perimeter 78, and can be made from ripstop nylon, for example. Under this embodiment, the lid is an upper covering, permanently attached to the perimeter of the receptacle 2 at its proximal end that is not configured to be opened, detached from its perimeter 78 (or alternatively a drawstring 42) or otherwise removed. While they both surround the lid or cover, the perimeter 78 is different from the drawstring 42 in that it cannot be tightened or loosened. In contrast, the central portion of the drawstring 42 is configured to tighten (shrink in diameter) when pulled outward and loosen (enlarge in diameter) when pulled inward. Preferably the drawstring 42 is made of a pliable material in addition having some elasticity. Under certain embodiments, pulling oppositely on the drawstring 42 and the distal cable 58 can collapse the receptacle.

According to certain embodiments the lid 46' has a central, or substantially central opening or aperture 68 that can be closed and opened. The central opening preferably has a center that is concentric with the center of the lid. The central opening 68 can be configured to be entirely closed or substantially so, such that at least 75% of the opening is closed. More specifically, the edges (66 and 72) can be approximated so that they are adjacent to or overlapping each other resulting in over 75% occlusion or closure of the central opening 68.

Likewise, the opening can be configured to be entirely open or substantially so, such that at least 75% of the opening is open. According to preferred embodiments, the central opening 68 is sized to allow a large specimen to be contained within the receptacle 2 and is thus larger than the premade holes 48, which are preferably configured to be used with trocars. The central opening can preferably be between 10-30 cms in length, for example. All lids described herein can be made of any suitable pliable material such as nylon (e.g., 7 denier ripstop), TYVEK®, or Ultra-High-Molecular-Weight Polyethylene, such as DYNEEMA®.

Figure 19:
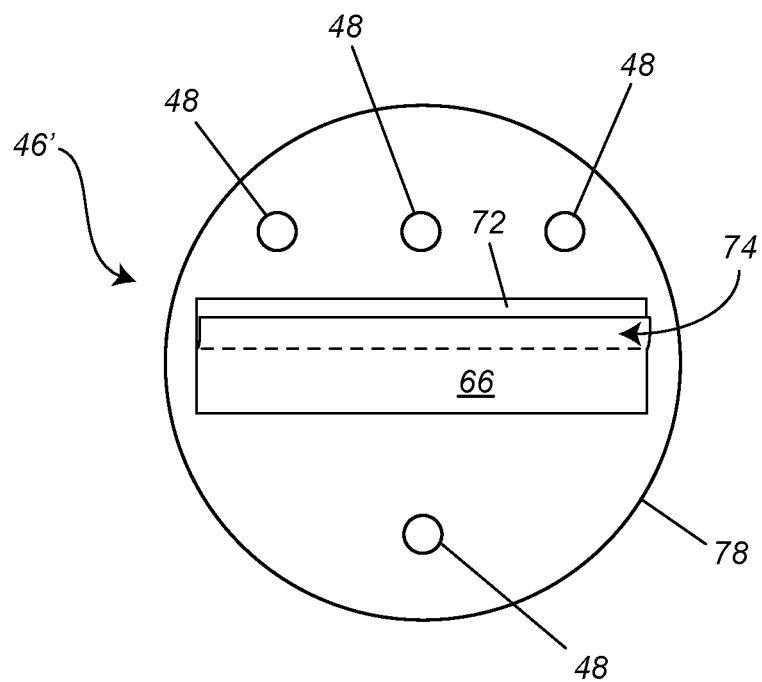
FIG. 19 shows a top view of another alternative lid.

As shown in FIG. 16, a flap 66 on the lid 46' can be configured to substantially or completely cover the central opening 68. The flap 66 can be releasably connected to the other side of the central opening 68 by any suitable means, including adhesives, buttons, snaps, or hook and loop fasteners, for example. In FIG. 16, the flap 66 can be secured by an adhesive, such as a wetness activated sealant, to the other side of the central opening 68. The wetness activated sealant can be made of a hydrophilic material such that when wetted (e.g., by saline), the cohesive bond can be formed with the other side of the central opening 68. FIG. 19 also shows the use of an adhesive or sealant. In this embodiment, the underside of the flap 66 includes a sealant/adhesive that binds with the topside of an under flap 72. The section of overlap 74 can be bound by the resulting cohesive bond. The over flap 66 and the under flap 72 can also be coupled by other mechanical, or non-adhesive ways, such as hook and loop fasteners, for example.

Figure 17:
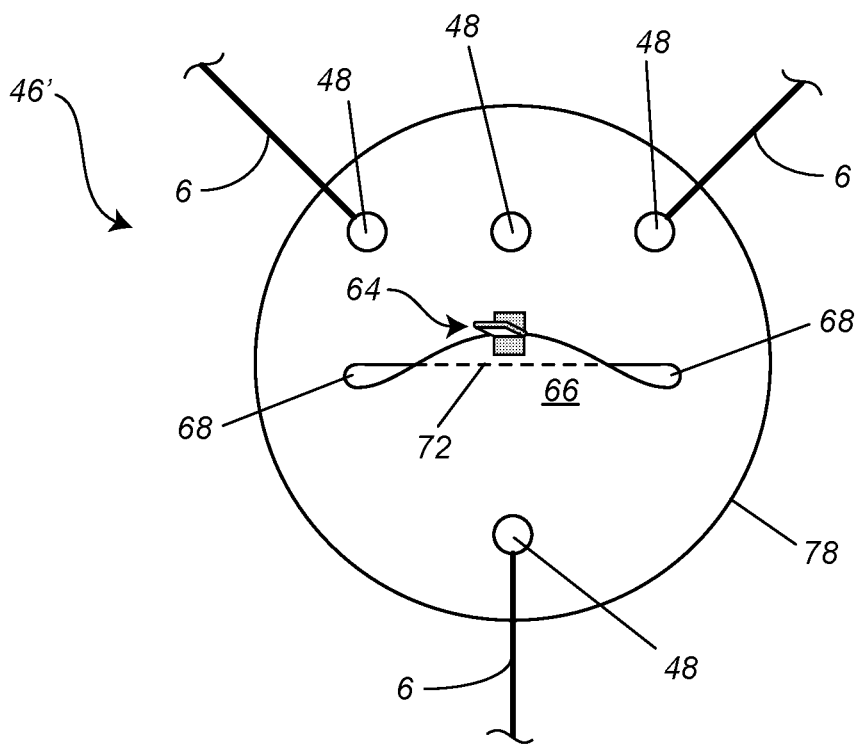
FIG. 17 shows a top view of another alternative lid.
Figure 18:
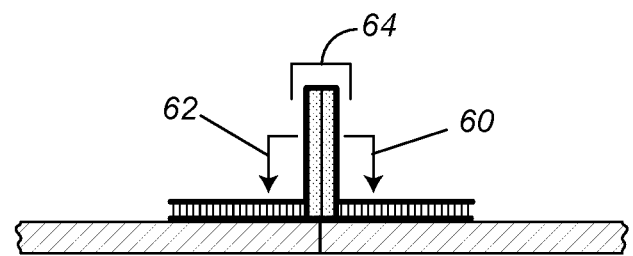
FIG. 18 shows a side view of a hook and loop fastener on a lid.

The flap 66 can also include a proximal protrusion/proximal extension member that extends proximally away from the lid 46' surface. For example, in FIG. 16 one or more loops 70 protrude proximally from the flap 66 or lid 46' and can be used by the practitioner to grasp and pull proximally, such as to extract the receptacle 2 from the patient. The loops 70 (and other suitable proximal extension members described herein) have an additional utility in that a practitioner can grasp one or more of them to keep the central opening 68 open, such as when they are placing the specimen 40 into the receptacle 2. Additionally, and as shown in FIGS. 17 and 18, hook 60 and loop 62 fasteners can be used to cover the central opening 68 to create a proximal protrusion tab 64. As one example, the loop 62 section can be positioned on the flap 66 and the hook 60 section can be positioned on the opposing side 72 of the central opening 68. These positions can be interchanged. The hook 60 and loop 62 fasteners can be used like the loops 70 described above. Specifically, they can be grasped and pulled proximally, such as to extract the receptacle 2 from the patient and the practitioner can grasp one or more (60 and 62) fasteners to keep the central opening 68 open, such as when they are placing the specimen 40 into the receptacle 2. FIG. 18 shows a slightly different embodiment than FIG. 17 in that two sides of the lid 46' are brought together by the hook 60 and loop 62 fasteners to close the central opening 68, instead of a flap 66 overlapping the central opening 68.

Figure 28:
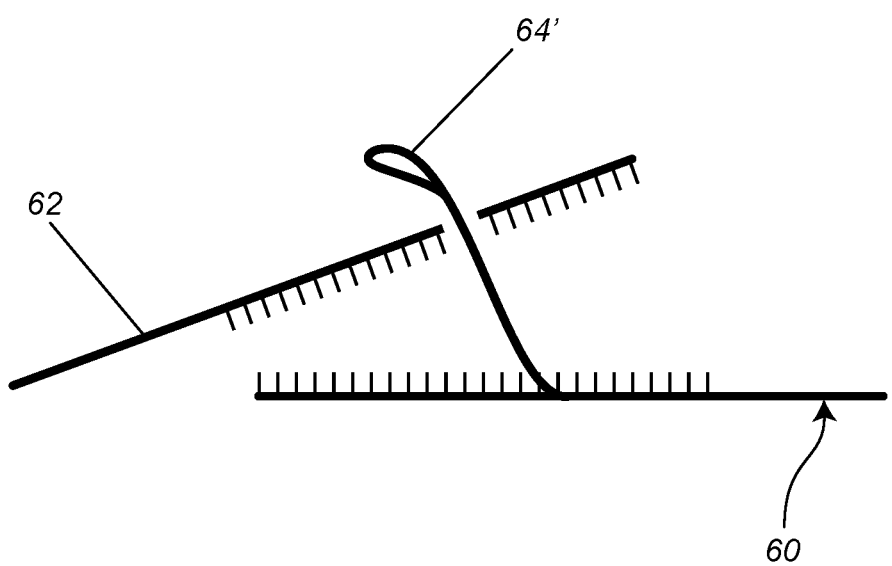
FIG. 28 shows an alternative hook and loop mechanism of closing a central slit on the lids.

Additionally, FIG. 28 shows another way of closing the central opening 68 by using hook 60 and loop 62 fasteners. In this embodiment, a proximal protrusion tab 64' extends upward from the hook 60 section through an aperture in the loop 62 section, these sections can be interchanged as well. In this embodiment, pulling up on the proximal protrusion tab 64' can close the hook 60 and loop 62 fasteners to each other. Further pulling on the proximal protrusion tab 64' can actuate the collapse of the receptacle 2 whether in conjunction with the simultaneous distal pulling of the distal cable 58 or by itself using an instrument through a trocar sleeve, for example.

These proximal protrusions/proximal extension members (e.g., loops 70, 84 and tabs 64) can be configured such that when pulled proximally they actuate the collapse of the receptacle 2 for passing through the trocar sleeve 10. Preferably these protrusions are centrally located on a non-detachable lid with an outer perimeter 78, (without a drawstring 42) and configured such that the simultaneous pulling of the distal cable 58 with the proximal pulling of these protrusions collapses the receptacle 2 so that it can pass through the trocar sleeve 10. The proximal protrusions can be made of either a rigid or pliable material. A further option, is to incorporate a distal cable 58 that can work in conjunction with the proximal protrusions to collapse the receptacle 2 when pulled distally simultaneously. This configuration can be used in lieu of a drawstring 42 for collapsing of the receptacle 2 for example. It is also envisioned to use a non-detachable lid 46' having a central opening 68 but lacking the premade holes 48 and instead having a penetrable material as in the membrane embodiments discussed herein. Further preferred embodiments are directed to lids 46' having premade holes 48 that are covered with a penetrable material and can be transparent. Preferred materials for the penetrable material include polyurethane, for example. Polyurethane film is advantageous in that it has some elasticity and so it can cling to the grasper (e.g., 28 and 38) that is passing through the hole 48. Preferred graspers can be between 5-10 mm in diameter, for example. Additionally, the premade holes 48 can be slits that are relatively closed with a thin opening that are widened/expanded when a trocar sleeve (e.g., 32) is inserted within. This embodiment helps prevent cut material from exiting the receptacle 2 through these oversized holes 48.

Figure 21:
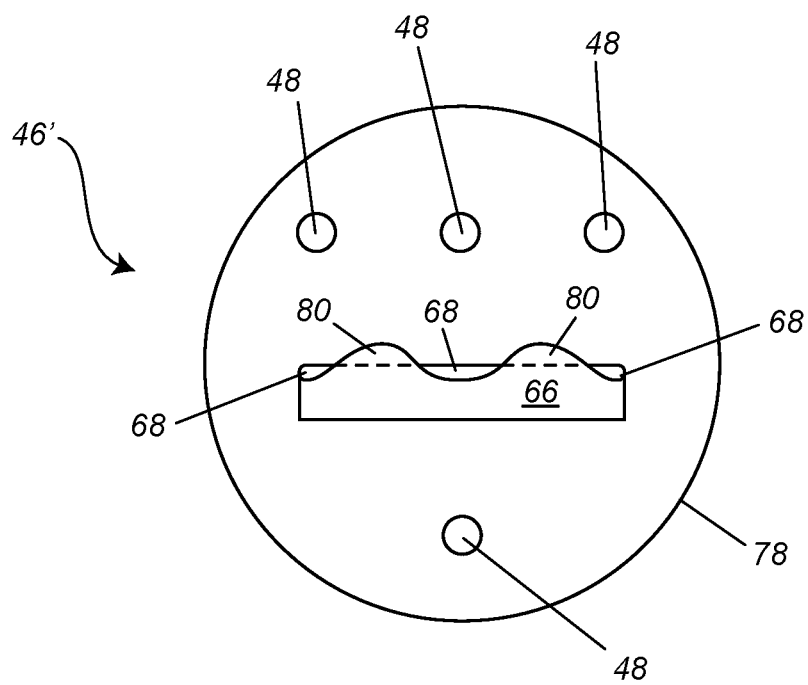
FIG. 21 shows a top view of another alternative lid.

FIG. 21 shows another lid 46' embodiment wherein the flap 66 is configured to intermittently overlap over the central opening 68. Under this embodiment, one or more sections 80 of the flap 66 extend to the other side of the central opening 68 and can be coupled accordingly to the embodiments described herein. According to more specific embodiments, the intermittent sections 80 can represent a sinusoidal wave exposing more areas of the central opening 68. Other flap 66 shapes can include a tongue shape, or straight, or other suitable configurations. The underside of the flap 66 can also include traction gripping members, such as checker plated, studded, or corrugated to increase friction and help maintain the closure over the central opening 68.

Figure 20:
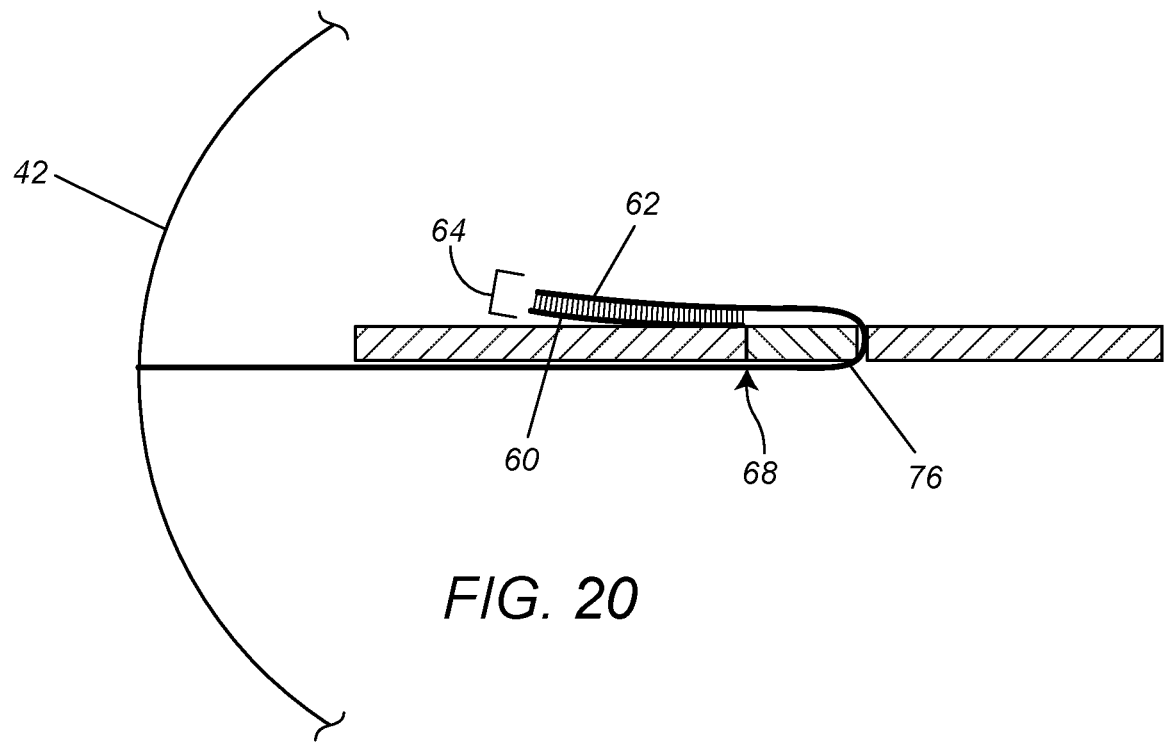
FIG. 20 shows a side view of a hook and loop fastener on a lid.

FIG. 20 shows a more intricate coupling mechanism for covering the central opening 68. According to this embodiment, a loop 62 section extends over the central opening 68 and couples to a hook 60 section on the other side to create a proximal tab 64. Preferably a thread 76 or other pliable elongated material is attached to the underside of the loop 62 section and traverses under the lid 46'. This configuration can be reversed such that the thread 76 is attached to the hook 60 section as well. This thread 76 or pliable material can be coupled to the draw string 42 of the lid 46'. According to certain embodiment, the draw string 42 can be rigid, elastic, or pliable, and can be made of nitinol according to further embodiments.

Figure 23:
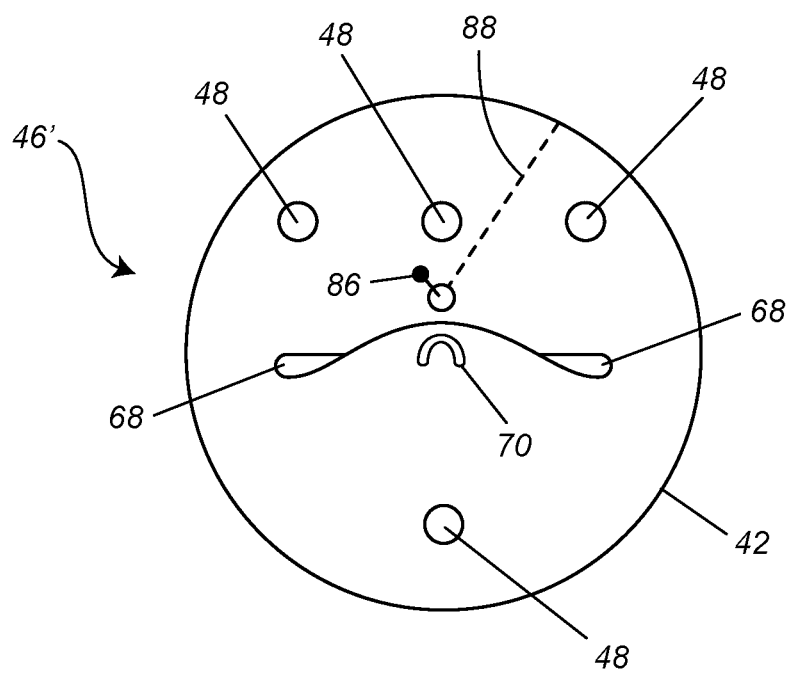
FIG. 23 shows a perspective top view of another alternative lid.

FIG. 23 shows a flap 66 covering most of the central opening 68 and having one or more loops 70 allowing a practitioner to more easily grasp, such as to open the central opening 68 to insert the specimen 40 and to pull proximally to extract the receptacle 2. This embodiment further utilizes a pull cord tab 86 that extends proximally from the lid 46' and configured to be grasped by the practitioner. The pull cord tab 86 is coupled to a taught pull cord 88 that is in turn coupled to the drawstring 42. The configuration is activated when the pull cord tab 86 is pulled, which in turns pulls the taught pull cord 88 towards the center of the lid 46' which then helps collapse the drawstring 42. The pull cord 88 can be passed through the one or more loops 70 and then proximally to collapse the receptacle 2. Collapsing the receptacle 2 is useful when the practitioner desires to extract the receptacle out of the patient.

Figure 24:
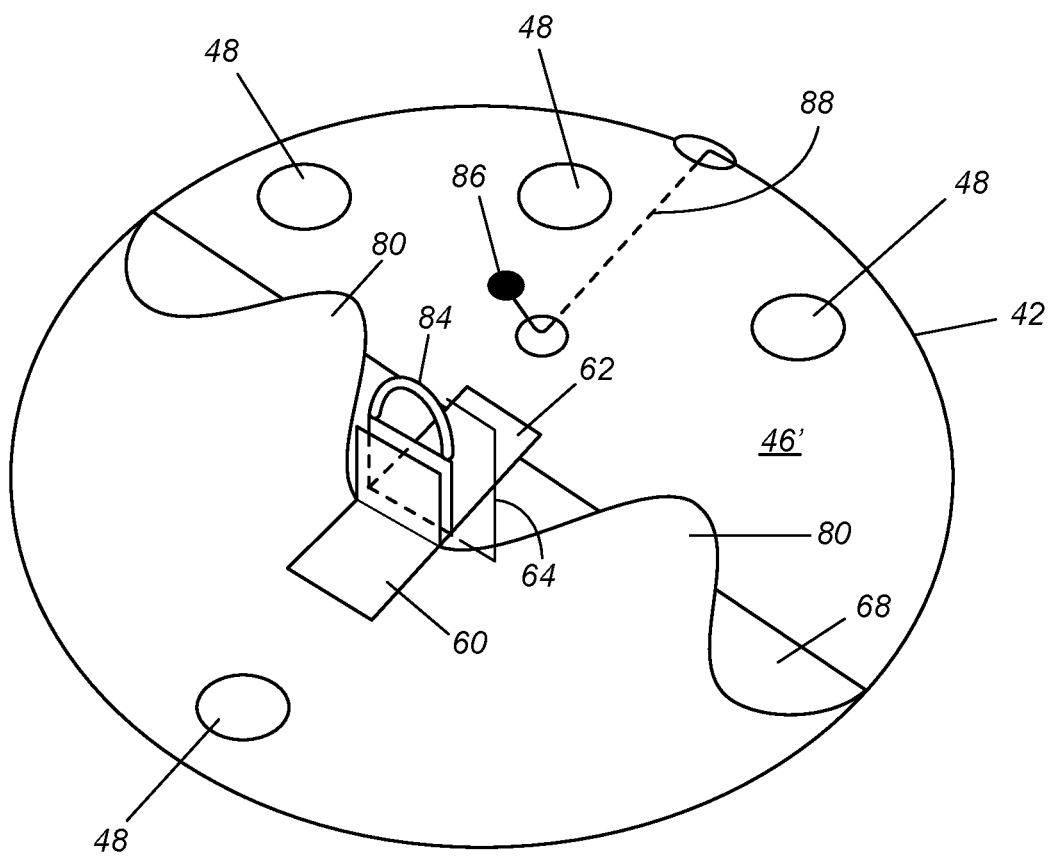
FIG. 24 shows a top view of another alternative lid.

FIG. 24 shows intermittent sections 80 of a flap 66 covering most of the central opening 68 and having a hook and loop fasteners 60 and 62 to couple together to form a proximal protrusion tab 64. Either the hook and/or loop section 60 and 62 can have a pull loop 84 to make the proximal protrusion tab 64 easier to grasp by an instrument when the practitioner wants to pull the receptacle 2 proximally. This embodiment further utilizes a pull cord tab 86 that extends proximally from the lid 46' and configured to be grasped by the practitioner. The pull cord tab 86 is coupled to a taught pull cord 88 that is in turn coupled to the drawstring 42. The configuration is activated when the pull cord tab 86 is pulled, which in turns pulls the taught pull cord 88 towards the center of the lid 46' which then helps collapse the drawstring 42. The pull cord 88 can be passed through the pull loop 84 and then proximally to collapse the receptacle 2. Collapsing the receptacle 2 is useful when the practitioner desires to extract the receptacle out of the patient.

Figure 29:
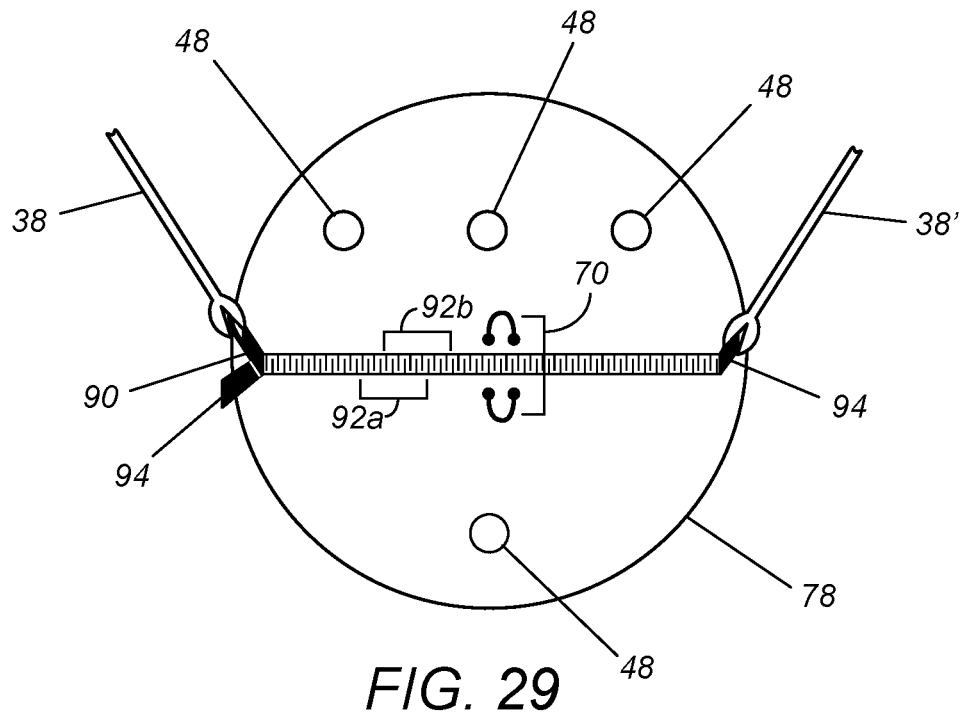
FIG. 29 shows a top view of a zippered lid in a closed configuration.
Figure 30:
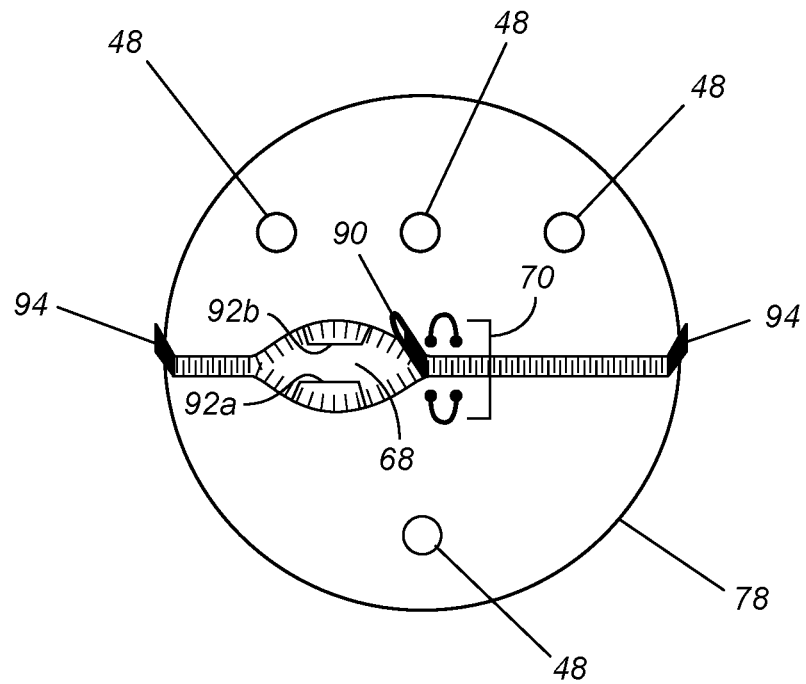
FIG. 30 shows a top view of a zippered lid as it is partially open.
Figure 31:
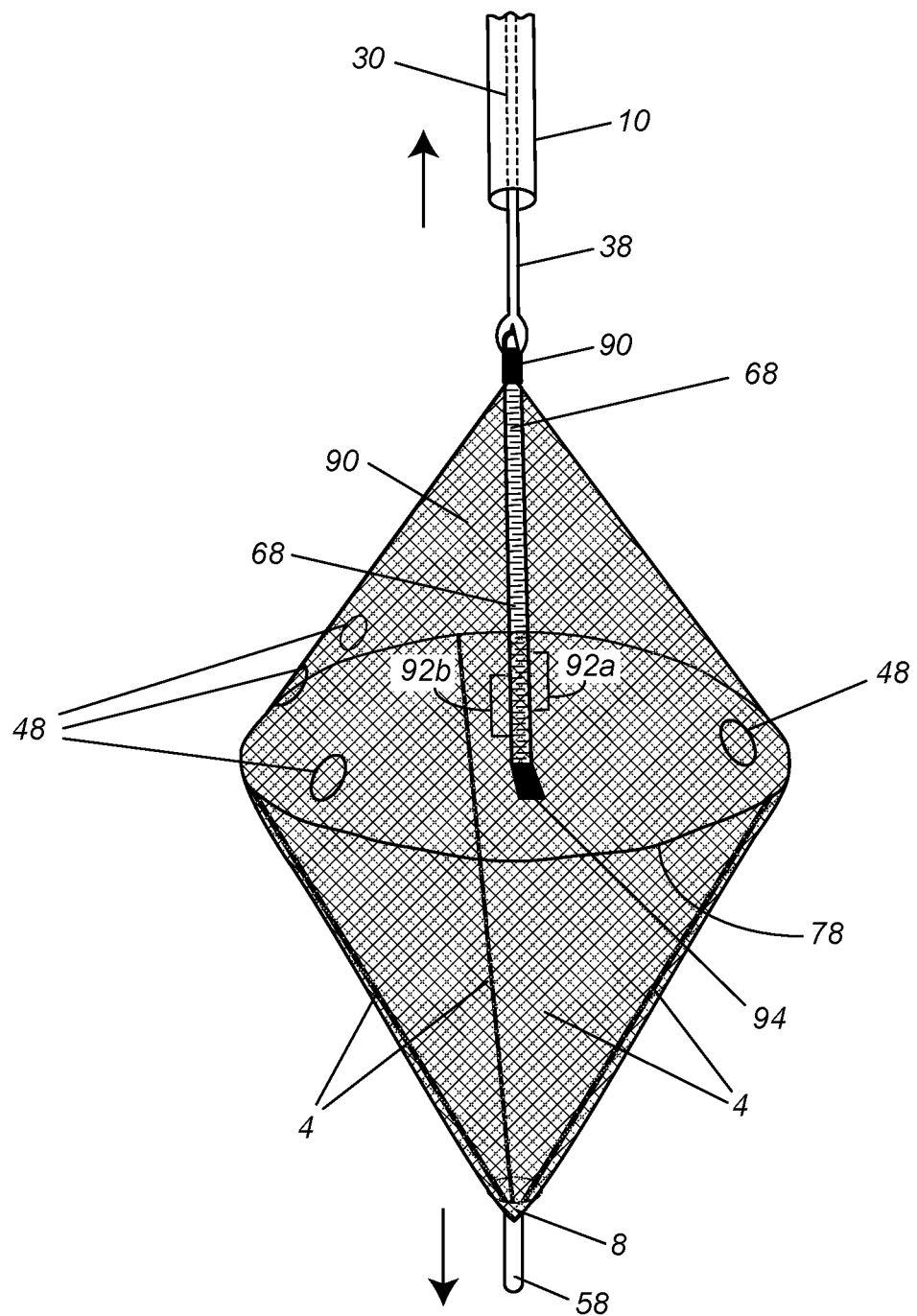
FIG. 31 shows a perspective view of a receptacle with a zippered lid being pulled proximally out of the patient through a trocar sleeve.

In addition to flaps, a zipper can be used to close or open the central opening 68. Non-exclusive examples of zippered lids 46' are shown in FIGS. 29-31. In FIG. 29, a first track of zipper teeth 92a runs parallel to and are engaged to a complementary second track of zipper teeth 92b thereby closing the central opening 68. Under this embodiment, the central opening 68 can be completely closed, such as during morcellation. A zipper slider 90 is operably coupled to both first and second tracks 92a and 92b that is configured to open and close the zipper by moving in a first and opposite direction respectively. Preferably the zipper slider 90 has a loop or tab extending from it that can be grabbed by a grasper (e.g., 38) to slide it more easily or to grab it to pull proximally to collapse and extract the receptacle 2 from the patient. The zipper slider 90 can be moved in either direction, depending on whether opening or closing, by utilizing any suitable instrument, such as grasping instrument 38 traversing through a trocar sleeve 10. According to preferred embodiments, in addition to the grasping instrument 38 controlling the slider 90 a second grasping instrument 38' can be used to pull the zipper away from the direction the slider 90 is moving, to provide resistance and make opening and closing easier. According to certain embodiments, one or more resistance tab/extensions 94 can be provided for the second grasping instrument 38' to pull against.

FIG. 30 shows the central opening 68 partially unzipped, but can be completely unzipped (e.g., opened) as well, such as when inserting or removing the specimen 40. Similarly, the central opening 68 can be closed after the specimen 40 is inserted and during morcelation. This helps prevent unwanted cut up bits of the specimen from traveling outside of the receptacle 2. A stop can be used to prevent the zipper slider 92 from undesirably contacting the lid 46' material. Preferred zipper teeth, sliders, and stops are made of a polymers or plastics. In addition to complementary tracks of zipper teeth, unless specified otherwise, the term "zipper" as used herein, also encompasses other non-teethed coupling profiles, such as rib and channel/groove mating incorporated in sandwich bags. Slider devices used for mating coupling profiles by moving in one direction and disengaging coupling profiles by moving in the opposite direction, such as used in sandwich bags, can likewise be used with these embodiments.

FIG. 31 shows a preferred way of collapsing and removing the receptacle 2 through the trocar sleeve 10. An instrument 30 extending through the distal opening of a trocar sleeve 10 can grasp any suitable proximal extending member such as the proximal protrusion tab 64, loop 70, zipper 90 or pull loop 84 and pull proximally towards the trocar sleeve 10. Preferably the proximal extending member is centrally located on the lid 46', or substantially so, to make collapsing of the lid 46' more uniform. According to further embodiments, the distal cable 58 can be simultaneously pulled distally with another instrument through another trocar sleeve to assist with collapsing the receptacle 2 such that it will fit through the trocar sleeve 10. According to these embodiments, no drawstring (42) is utilized, rather the lid 46' has an outer perimeter 78. Additionally, when the one or more proximal extending members (e.g., loops 70) are pulled proximally, the receptacle is configured to collapse such that its diameter that can fit through the trocar 10 for extraction. According to more specific embodiments, the collapsing of the receptacle 2 during insertion can be facilitated as the expanded sides of the receptacle 2 are pushed into the proximal end of the trocar sleeve 10. Similarly, the collapsing of the receptacle 2 during extraction can be facilitated as the one or more proximal extending members on the lid 46' are pulled proximally, and the pulled lid 46' is pulled into the distal end of the trocar sleeve 10. This is preferably done while the distal cable 58 is simultaneously pulled in a distal direction.

Figure 25:
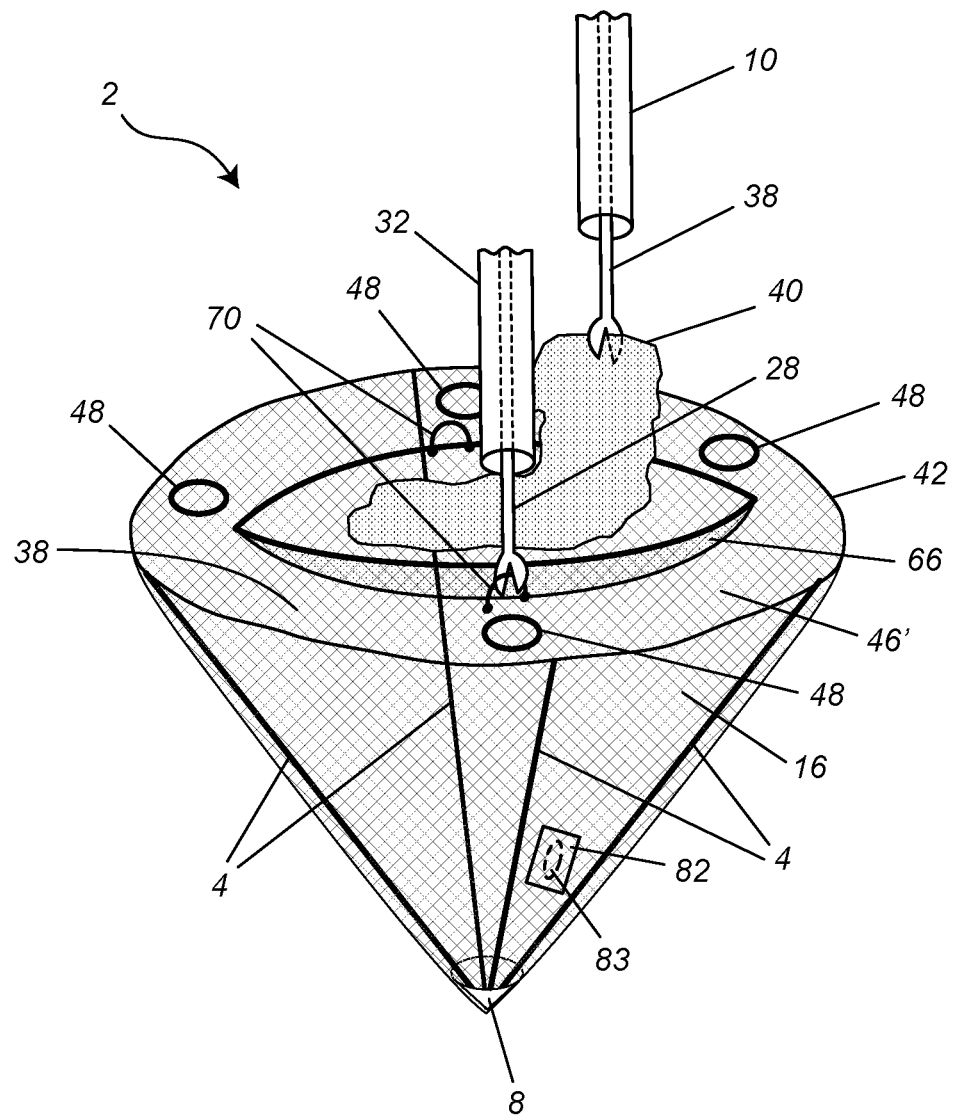
FIG. 25 shows a top perspective view of a specimen being inserted through a closable central opening within a lid.

FIG. 25 shows a top perspective view of a specimen 40 being inserted through a closable central opening 68 within a lid 46'. A grasping instrument 28 is fitted through a trocar sleeve 32 and exposes the central opening 68 (by either grasping the flap 66 or the loop 70, as shown in FIG. 25), to allow the specimen 40 to be inserted into the receptacle 2 by another instrument 38 inserted through a trocar sleeve 10. According to further embodiments, the receptacle 2 can include a valve 83 to release air from within to aid with collapsing. The air can be released through the valve 83 as the receptacle 2 is collapsing. According to preferred embodiments, the valve 83 can be a one-way exhaust valve, such as a simple loose covering of pliable material 82 over a hole or a slit in the receptacle. More specifically the sides of the of the pliable material 82 covering can be attached to the receptacle 2 to allow air to be released from the valve 83 such as along 1-3 of its sides, but not sealed along all four sides. If the valve covering is another shape than a quadrilateral, not all of its perimeter will be sealed to the receptacle. The valve 83 can be located on any suitable spot in the receptacle 2 but is preferably located near the distal base 8.

Figure 22:
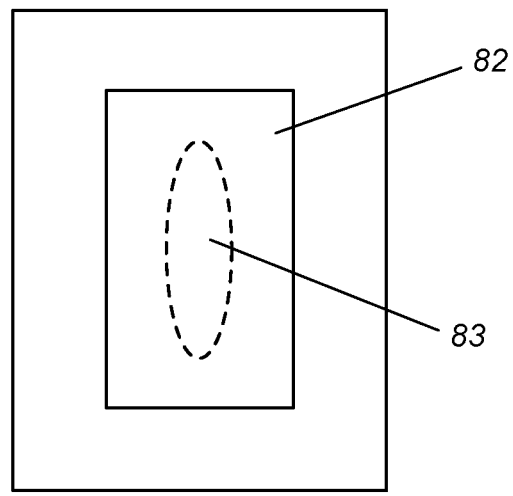
FIG. 22 shows a valve for releasing air within the receptacle.

According to more detailed embodiments, the valve 83 is between 2-10 cms from the distal base, such as at about 4 cm from the distal base. According to these embodiments, as the proximal and middle sections of receptacle 2 are being pulled out of the patient through the sleeve 10, the air within the receptacle 2 can be released through the valve 83, such as when the lid 46' is pressed against the distal end of the trocar sleeve 10. FIG. 22 provides a close-up view of a preferred valve 83 and covering 82.

Furthermore, the receptacle 2 can be designed to collapse in height alone, so that there is more room and visibility to place the specimen 40 inside the container prior to morcellation and to better accommodate the bag inside the cavity. Once the specimen 40 is placed in the receptacle the opening can be pulled upward (proximally) lengthening the height in preparation for the morcellation. During power morcellation each cut tissue is limited to a maximum diameter so that they can easily fit through a trocar sleeve of a slightly larger diameter. The procedure is for removal of the cut tissue through the specified sleeve during or after morcellation of the tissue, but prior to the removal of the receptacle 2. The distal end of the morcellator and the sleeve, from which the tissue will be removed, are within the opening of the receptacle, so that no pieces of cut tissue inadvertently fall outside the receptacle and into the abdominal cavity. Once the specimen has been cut and all the cut pieces removed, the empty bag is collapsed and removed out the same tissue removing sleeve.

Prior to its use, the receptacle can be stored inside a tube that can be used as the trocar sleeve at the time of morcellation. Alternatively, the tube, storing the receptacle, can hold the receptacle in its collapsed position as the receptacle is being inserted through a trocar sleeve previously inserted. According to preferred embodiments, there is a tubular ring around the receptacle, keeping it collapsed. This ring has a larger diameter than the inside of the trocar sleeve. Through its center is a pushrod, the pushrod can be configured to push the collapsed receptacle into the trocar sleeve and then through the tubular ring and trocar sleeve.

Insertion of the receptacle 2 into the patient's body, such as the abdominal cavity, can be accomplished any suitable way, such as by pushing the proximal ends of the collapsed support rods 4 through the hollow channel of the trocar sleeve 10 and out the distal opening 14. Preferably insertion is by pushing the distal end with base 8 though the proximal end of the sleeve 10 thereby collapsing the rods 4 and receptacle 2. Removal of the receptacle 2 through the proximal opening 22 of the trocar sleeve 10 can be done using any suitable way. As one non-limiting example, a medical practitioner can inwardly pull on filaments 6 attached to the receptacle 2 and positioned outside of the patient's body. Preferably, removal is by pulling on the drawstring 42 on the proximal end through the sleeve 10, thereby collapsing the receptacle 2, so that the receptacle can be pulled out proximal end first. According to further embodiments, the distal cap 8 of the receptacle can be attached to a distal cable 58 that a practitioner can pull on from inside the cavity to aide in the insertion of the receptacle 2. While the receptacle 2 is configured to be inserted distal end 8 first, according to certain embodiments it can be extracted either distal 8 or proximal end 18 first. For example, after closing the drawstring 42, the receptacle can be inverted and pulled up by the distal end first without spilling the contents of the receptacle 2.

For embodiments utilizing the attached lid 46', certain embodiments entail a user pulling proximally on the central tabs or loops (e.g., 70, 64, 84) on the lid 46' through a trocar sleeve (e.g., 10) and simultaneously pull distally on the distal cable 58. Alternatively, grasping and pulling the pull cord tab 86 through the pull loop 84 will both tighten the drawstring 42 and simultaneously pull the central section of the lid through the trocar sleeve 10.

Figure 26:
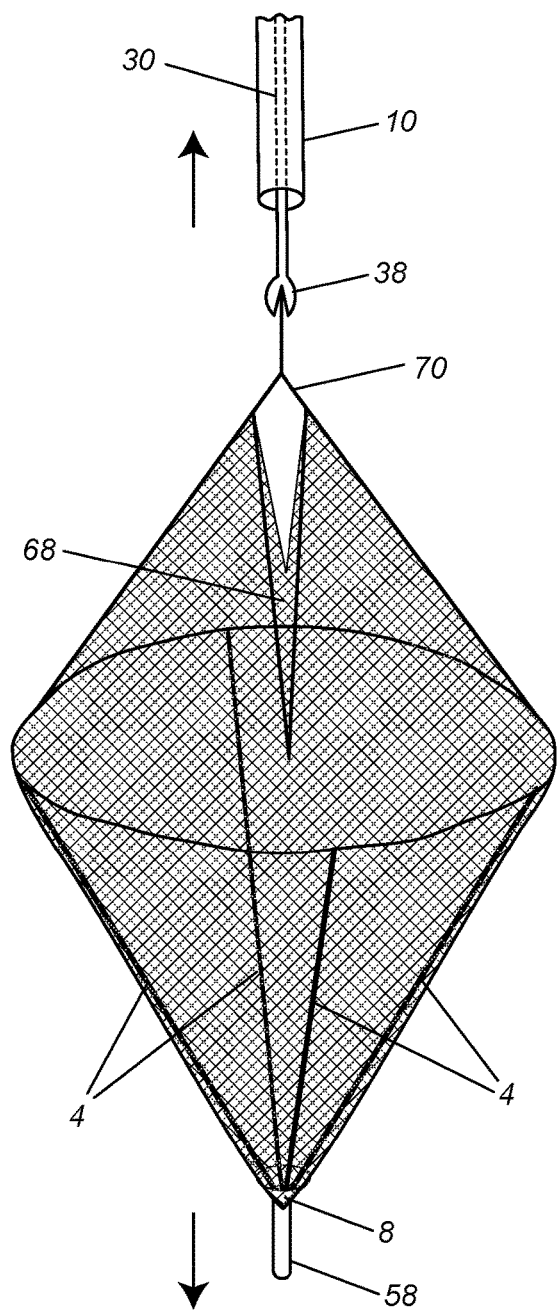
FIG. 26 shows a perspective view of a receptacle being pulled proximally out of the patient through a trocar sleeve.
Figure 27:
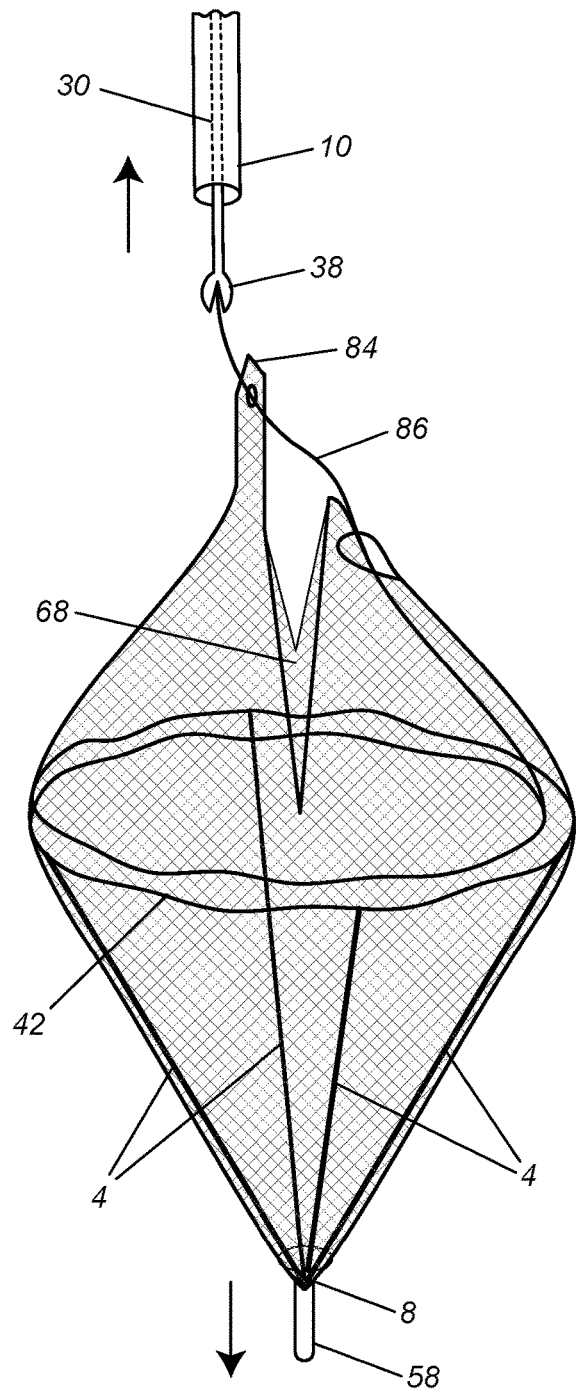
FIG. 27 shows a perspective view of an alternate receptacle being pulled proximally out of the patient through a trocar sleeve.

FIG. 26 shows a preferred way of collapsing and removing the receptacle 2 through the trocar sleeve 10. An instrument 30 extending through the distal opening of a trocar sleeve 10 can grasp a proximal extension member such as a protrusion tab 64, loop 70 or pull loop 84 and pull proximally towards the trocar sleeve 10. According to further embodiments, the distal cable 58 can be simultaneously pulled distally with another instrument through another trocar sleeve to assist with collapsing the receptacle 2 such that it will fit through the trocar sleeve 10.

Preferred methods of morcellating a targeted piece of tissue in a subject include: a) providing a morcellation receptacle as described herein b) creating an incision in the subject near the targeted piece of tissue, wherein the incision has a width of between 14-20 mm and inserting a trocar sleeve into the incision; c) collapsing the receptacle; d) inserting the collapsed receptacle inside of the subject through the trocar sleeve; e) opening the central opening on the permanent lid of the receptacle; f) positioning the targeted tissue into the receptacle through the central opening, then closing said central opening such that cut pieces of the targeted tissue will remain within the receptacle; g) positioning a morcellator into the proximal opening of the receptacle and cutting the target tissue; h) removing the cut targeted tissue from the receptacle through the trocar sleeve; and i) collapsing the receptacle and withdrawing it from inside the subject through the trocar sleeve.

According to preferred embodiments, the targeted specimen 40 has been previously detached from its original points of attachment to the patient, so that it can be positioned into the open receptacle 2.

The preferred methods of use of the teachings herein are for laparoscopic surgery and are directed for the morcellation receptacle 2 to be collapsed and pushed through a first trocar sleeve 10 that has a diameter of 14 to 20 mm and has been placed through the anterior wall into the patient's cavity where it self-expands open, through natural spring tension, into its natural, open position. The targeted specimen 40 that has been previously detached from its points of attachment is positioned into the open receptacle 2 through the proximal opening 18. The lid 46 can then be collapsed and pushed through the trocar sleeve 10 into the cavity, where it self-expands, and is positioned on top of the proximal opening 18 of the receptacle 2. According to other embodiments, the lid 46' or membrane 54 is already attached to the receptacle 2 so they are inserted as one-piece. A rod or other instrument can be used to push the receptacle 4 into and through the trocar sleeve 10. Afterwards, the specimen 40 is placed into the receptacle 2 through the exposed central opening 68, the central opening is then closed according to any of the suitable embodiment, such as those described herein, and the specimen 40 is then morcellated within the closed receptacle 2.

The proximal ends of the receptacle 2 has (3 or 4) filaments 6 attached at their distal ends. The proximal ends of the filaments 6 are grasped through the openings 48 of the lid 46, and pulled proximally through the anterior wall 12, on the outside perimeter and adjacent to the trocar sleeves 10, 32, 34, and 36 that have been previously inserted. Pulling the filaments 6 more proximal pulls the receptacle 2 with specimen 40 inside, and lid 46 on top proximally toward the inside of the anterior wall 12. The filament 6 sections positioned outside the cavity and proximal to the anterior wall are clamped with clamps 26 so that the receptacle 26 is immobilized or substantially so. The distal end 14 of the first trocar sleeve 10 is positioned through the corresponding hole 48/50 of the lid 46 and positioned so that its distal segment extends into the bag. The second, third and if necessary 4th trocar sleeves 32, 34, and, 36 are positioned through their corresponding lid openings 48/50 with their distal segments positioned inside the bag. According to further embodiments, the filaments 6 can be released from the clamps 26, and then the receptacle 2 and attached lid 46' or membrane 54 are removed as one piece, by pulling, proximally, on the filaments 6 on the center portion of the lid 43' through the sleeve, and pulling distally on the filament extending from the base of the receptacle, and alternatively, if present, pulling on the drawstring prior to or simultaneously.

As shown in FIG. 15, the proximal ends of the receptacle 2 can also have three filaments 6 attached to the bag at their distal ends. At their proximal ends, the filaments 6 are grasped through the openings of the lid and pulled proximally through the anterior abdominal wall 12 on the outside perimeter and adjacent to the trocar sleeves 32, 34, and 36 that have been previously inserted. The distal end 14 of the first trocar sleeve 10 is positioned through its corresponding hole.

The electric morcellator 28 is then inserted through second trocar sleeve 32 so that the blade is inside the receptacle 2 and adjacent to the specimen 40 to be cut. For visualization, a laparoscope is inserted through any suitable trocar sleeve 36, and a first grasper 38 can be inserted through first trocar sleeve 10 and a second grasper 30 can be inserted through a fourth trocar sleeve 34 to stabilize the specimen 40 during morcellation. The morcellated pieces are individually removed from the bag through first trocar sleeve 10, from which the receptacle 2 itself is inserted and extracted though, which preferably has a larger diameter than the other trocar sleeves. Once the receptacle 2 is empty, the morcellator 28 and graspers 30 and 38 are removed through their respective trocar sleeves 34 and 10. Additionally the laparoscope is removed from its trocar sleeve 36. According to preferred embodiments, the laparoscope with corresponding trocar sleeve 36 can remain inside the cavity to maintain visualization as the lid 46 and receptacle 2 are removed. The filaments 6 are released from the clamps 26. The lid 46 is collapsed and removed through the first trocar sleeve 10. The drawstring 42 on the proximal end of the bag is pulled into and through first trocar sleeve 10, collapsing the receptacle 2. The receptacle 2 is then removed through the first trocar sleeve 10. Alternatively, if the morcellator has a larger diameter requiring it to slide through trocar 10, then cut pieces are left in the bag until the desired time to remove them. According to this embodiment, the morcellator can then be removed from the trocar sleeve 10 sleeve and the grasper 38 could be used to remove the cut pieces individually through the trocar sleeve 10.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A morcellation receptacle system comprising:
a collapsible and expandable receptacle, having a vertical axis with a lower half section with a distal area, and an upper half section with a proximal end, and a horizontal axis, configured such that when the collapsible receptacle is collapsed on its horizontal axis, it is linearly sized to fit within and through an opening between 14-20 mm in width but not when expanded in a natural open position; said receptacle comprising:
a plurality of at least three support rods positioned in a circumferential and equidistant manner around the vertical axis, or substantially so, having distal ends coupled to the distal area of the receptacle and having proximal ends extending proximally and laterally away from the distal area and configured to have natural spring tension such that the support rods are expanded, away from each other in a natural, open, position, and move towards each other on the horizontal axis when the receptacle is collapsing and move away from each other on the horizontal axis when the receptacle is opening,
a flexible liner that is water resistant, low-friction, tear-resistant, and made of material different from the support rods, having a thickness between 0.05-0.15 mm, wrapped along the support rods such as to define a bag with a closed end at the distal area;
and a cover made of a thin flexible material that is permanently attached to a perimeter of the proximal end of the receptacle, such that the cover and the perimeter of the proximal end of the receptacle are expandable and collapsible to fit through the 14 to 20 mm opening and the cover establishes a surface area having a plurality of premade holes configured to allow a trocar sleeve to pass through into the receptacle along the vertical axis when the receptacle is in a natural expanded position, and wherein the cover comprises a substantially central opening configured to be releasably closable, such that at least 75% of area of the substantially central opening is occluded, while the perimeter of the proximal end of the receptacle is maintained in its expanded natural, open position and the plurality of premade holes individually remain accessible for the trocar sleeve to pass through into the receptacle along the vertical axis.

2. The morcellation receptacle system of claim 1, further comprising complementary sides of the substantially central opening that are configured to releasably bind with each other to close and open the substantially central opening.

3. The morcellation receptacle system of claim 2, wherein the cover comprises two zippered tracks configured to be opened and closed by a zipper slider.

4. The morcellation receptacle system of claim 1, wherein the cover further comprises a proximal extending member and the distal area comprises a distal extending member configured such that when both are simultaneously pulled proximally and distally, respectively, the receptacle collapses from its expanded natural open position.

5. The morcellation receptacle system of claim 4, wherein the proximal extending member is selected from the group consisting of: a proximal protrusion tab, a loop, zipper slider, and a pull loop.

6. The morcellation receptacle of claim 1, further comprising a one-way release valve positioned on the flexible liner configured to allow gas to escape from the receptacle.

7. The morcellation receptacle system of claim 1, wherein the perimeter of the proximal end of the receptacle comprises a drawstring configured to collapse the receptacle from its expanded position when pulled away from the perimeter.

8. The morcellation receptacle system of claim 1, wherein the cover's surface area is a substantially flat surface area along the horizontal axis.

9. A method of morcellating a targeted piece of tissue in a subject comprising:
   a) providing a collapsible and expandable receptacle, having a vertical axis with a lower half section with a distal area, and an upper half section with a proximal end, and a horizontal axis, configured such that when the collapsible receptacle is collapsed on its horizontal axis, it is linearly sized to fit within and through an opening between 14-20 mm in width but not when expanded in a natural open position; said receptacle comprising:
   a plurality of at least three support rods positioned in a circumferential and equidistant manner around the vertical axis, or substantially so, having distal ends coupled to the distal area of the receptacle and having proximal ends extending proximally and laterally away from the distal area and configured to have natural spring tension such that the support rods are expanded, away from each other in a natural, open, position, and move towards each other on the horizontal axis when the receptacle is collapsing and move away from each other on the horizontal axis when the receptacle is opening,
   a flexible liner that is water resistant, low-friction, tear-resistant, and made of material different from the support rods, having a thickness between 0.05-0.15 mm, wrapped along the support rods such as to define a bag with a closed end at the distal area;
   and a cover made of a thin flexible material that is permanently attached to a perimeter of the proximal end of the receptacle, such that the cover and the perimeter of the proximal end of the receptacle are expandable and collapsible to fit through the 14 to 20 mm opening and the cover establishes a surface area having a plurality of premade holes configured to allow a trocar sleeve to pass through into the receptacle along the vertical axis when the receptacle is in a natural expanded position, and wherein the cover comprises a substantially central opening configured to be releasably closable, such that at least 75% of area of the substantially central opening is occluded, while the perimeter of the proximal end of the receptacle is maintained in its expanded natural, open position, and the plurality of premade holes individually remain accessible for the trocar sleeve to pass through into the receptacle along the vertical, axis;
   b) creating one or more incisions in the subject near the targeted piece of tissue, wherein the incision has a width of between 14-20 mm and inserting a first trocar sleeve into a first incision;
   c) collapsing the receptacle;
   d) inserting the collapsed receptacle inside of the subject through the first trocar sleeve;
   e) positioning the targeted tissue into the receptacle through the substantially central opening in the cover;
   f) closing the substantially central opening such that at least 75% of the opening's area is occluded;
   g) positioning a morcellator into the receptacle and cutting the target tissue;
   h) removing the cut targeted tissue from the receptacle through a trocar sleeve; and
   i) collapsing the receptacle and withdrawing it from inside the subject through a trocar sleeve.

10. The method of claim 9, wherein the cover further comprises complementary sides of the substantially central opening that are configured to releasably bind with each other to close and open the central opening.

11. The method of claim 10, wherein the cover comprises two zippered tracks configured to be opened and closed by a zipper slider.

12. The method of claim 9, wherein the cover further comprises a proximal extending member and the distal area comprises a distal extending member configured such that when both are simultaneously pulled proximally and distally, respectively, the receptacle collapses from its expanded natural open position.

13. The method of claim 12, wherein the proximal extending member is selected from the group consisting of: a proximal protrusion tab, a loop, zipper slider, and a pull loop.

14. The method of claim 9, further comprising a one-way release valve positioned on the flexible liner configured to allow gas to escape from the receptacle.

15. The method of claim 9, wherein the perimeter of the proximal end of the receptacle comprises a drawstring configured to collapse the receptacle from its expanded position when pulled away from the perimeter.

16. A morcellation receptacle system comprising:
   a collapsible and expandable receptacle, having a vertical axis with a lower half section with a distal area, and an upper half section with a proximal end, and a horizontal axis, configured such that when the collapsible receptacle is collapsed on its horizontal axis, it is linearly sized to fit within and through an opening between 14-20 mm in width but not when expanded in an expanded, open position; said receptacle comprising:
   a flexible liner that is water resistant, low-friction, tear-resistant, having a thickness between 0.05-0.15 mm, that defines a bag with a closed end at the distal area;
   a cover made of a thin flexible material that is permanently attached to a perimeter of the proximal end of the receptacle, such that the cover and the perimeter of the proximal end of the receptacle are expandable and collapsible to fit through the 14 to 20 mm opening and the cover establishes a surface area having a plurality of premade holes configured to allow a trocar sleeve to pass through into the receptacle along the vertical axis when the receptacle is in its expanded open position, and wherein the cover comprises a substantially central opening configured to be releasably closable, such that at least 75% of area of the substantially central opening is occluded, while the perimeter of the proximal end of the receptacle is maintained in its expanded, open position, and the plurality of premade holes individually remain accessible for the trocar sleeve to pass through into the receptacle along the vertical axis; and a plurality of at least two support filaments having distal ends coupled to the upper half section of the receptacle in a circumferential manner and configured such that when proximal ends of the support filaments are pulled away from each other, the receptacle is moved in a proximal direction and is maintained in an open position.

17. The morcellation receptacle system of claim 16, wherein at least two of the premade holes have adjacent support filaments positioned to allow alignment between the trocar sleeves with the premade holes to allow for easier insertion of the trocar sleeves into the receptacle.

18. The morcellation receptacle system of claim 16, further comprising a plurality of support rods positioned in a circumferential and equidistant manner around the vertical axis, or substantially so, having distal ends coupled to the distal area of the receptacle and having proximal ends extending proximally and laterally away from the distal area and configured to have natural spring tension such that the support rods are expanded, away from each other in a natural position, and move towards each other on the horizontal axis when the receptacle is collapsing and move away from each other on the horizontal axis when the receptacle is opening.

* * * * *